United States Patent
Tsuzuki et al.

(10) Patent No.: US 8,367,835 B2
(45) Date of Patent: Feb. 5, 2013

(54) CYCLIC AMINE-1-CARBOXYLIC ACID ESTER DERIVATIVE AND PHARMACEUTICAL COMPOSITION CONTAINING THE SAME

(75) Inventors: Yasunori Tsuzuki, Suita (JP); Toshiya Morie, Osaka (JP); Takanori Nakamura, Suita (JP); Isao Shimizu, Suita (JP); Masanori Miyauchi, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 273 days.

(21) Appl. No.: 12/991,224

(22) PCT Filed: May 7, 2009

(86) PCT No.: PCT/JP2009/058644
§ 371 (c)(1),
(2), (4) Date: Nov. 5, 2010

(87) PCT Pub. No.: WO2009/136625
PCT Pub. Date: Nov. 12, 2009

(65) Prior Publication Data
US 2012/0028937 A1 Feb. 2, 2012

(30) Foreign Application Priority Data
May 7, 2008 (JP) ................. 2008-121701

(51) Int. Cl.
A61K 31/445 (2006.01)
C07D 211/26 (2006.01)
(52) U.S. Cl. .................... 546/229; 514/328
(58) Field of Classification Search ............. 546/229; 514/328
See application file for complete search history.

(56) References Cited

U.S. PATENT DOCUMENTS

| 7,615,557 B2 | 11/2009 | Bouchon et al. |
| 2004/0248983 A1 | 12/2004 | Morie et al. |
| 2007/0135423 A1 | 6/2007 | Bayliss et al. |
| 2007/0167458 A1 | 7/2007 | Bouchon et al. |
| 2009/0082463 A1 | 3/2009 | Morie et al. |
| 2009/0105258 A1 | 4/2009 | Kim et al. |

FOREIGN PATENT DOCUMENTS

| EP | 1 403 235 | 3/2004 |
| JP | 2005-504074 | 2/2005 |
| JP | 2007-502258 | 2/2007 |
| JP | 2007-508255 | 4/2007 |
| JP | 2007-509915 | 4/2007 |
| WO | 2002/100819 | 12/2002 |
| WO | 03/022809 | 3/2003 |
| WO | 2004/087646 | 10/2004 |
| WO | 2005/016915 | 2/2005 |
| WO | 2005/040119 | 5/2005 |
| WO | 2005/051390 | 6/2005 |
| WO | 2006/101318 | 9/2006 |
| WO | 2007/003962 | 1/2007 |
| WO | 2008/110008 | 9/2008 |

OTHER PUBLICATIONS

European Search Report issued Jul. 10, 2012 in corresponding European Application No. 12 166 546.7.
International Search Report issued Jun. 9, 2009 in International (PCT) Application No. PCT/JP2009/058644.
Michael J. Caterina et al., "The Capsaicin Receptor: A Heat-Activated Ion Channel in the Pain Pathway", Nature, vol. 389, Oct. 23, 1997, pp. 816-824.
Michael J. Caterina et al., "The Vanilloid Receptor: A Molecular Gateway to the Pain Pathway", Annu. Rev. Neurosci., vol. 24, 2001, pp. 487-517.
Arpad Szallasi et al., "Vanilloid (Capsaicin) Receptors and Mechanisms", Pharmacological Reviews, vol. 51, No. 2, 1999, pp. 159-211.
Stephen H. Buck et al. "The Neuropharmacology of Capsaicin: Review of Some Recent Observations", Pharmacological Reviews, vol. 38, No. 3, 1986, pp. 179-226.
Dorte X. Gram et al., "Plasma Calcitonin Gene-Related Peptide is Increased Prior to Obesity, and Sensory Nerve Desensitization by Capsaicin Improves Oral Glucose Tolerance in Obese Zucker Rats" European Journal of Endocrinology, vol. 153, 2005, pp. 963-969.
Form PCT/IB/338 together with International Preliminary Report on Patentability including translation of PCT Written Opinion dated Dec. 23, 2010 in corresponding International application No. PCT/JP2009/058644.

*Primary Examiner* — Janet Andres
*Assistant Examiner* — John Mabry
(74) *Attorney, Agent, or Firm* — Wenderoth, Lind & Ponack, L.L.P.

(57) ABSTRACT

Provided is a compound useful as a therapeutic drug for pain and inflammation caused by various pathological conditions such as neuropathic pain and rheumatoid arthritis. The compound of the formula (I) or a salt thereof [wherein $R^1$ is a methyl group or a hydrogen atom, $R^2$ represents a hydrogen atom, an alkyl group, an alkylcarbonyl group or an aryl carbonyl group, A represents a cycloalkyl group, a cycloalkenyl group, an aryl group or a heteroaryl group (each group may be substituted with a substituent selected from the group consisting of alkyl, alkenyl, cycloalkyl and halogen), n and m each represent an integer of 1, 2 or 3, and p represents an integer of 0, 1, 2 or 3].

[Chemical Formula 1]

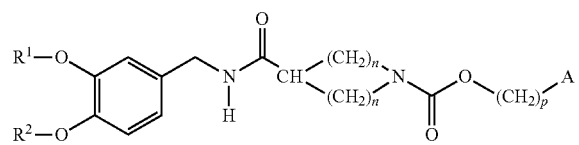

(I)

19 Claims, No Drawings

CYCLIC AMINE-1-CARBOXYLIC ACID ESTER DERIVATIVE AND PHARMACEUTICAL COMPOSITION CONTAINING THE SAME

TECHNICAL FIELD

The present invention relates to a cyclic amine-1-carboxylic acid ester derivative useful as a therapeutic drug for pain and inflammation, and more particularly, to a cyclic amine-1-carbocylic acid ester derivative having a 3,4-disubstituted benzyl carbamoyl group on the cycle and a pharmaceutical composition containing the same.

BACKGROUND ART

At present, narcotic analgesics such as morphine and non-narcotic analgesics such as NSAIDs (Non-Steroidal Anti-Inflammatory Drugs) are primarily used as analgesics. However, narcotic analgesics express tolerance, addiction or other severe side-effects, and use thereof is hence heavily restricted. Also, NSAIDs are not effective for an severe pain and pose additional problems of causing the upper gastrointestinal tract disorder and liver disorder at a high rate when administered for an extended period of time. For these reasons, analgesics with a higher analgesic effect and fewer adverse reactions are demanded. Further, a highly satisfactory analgesic is not yet found for neuropathic pains such as diabetic neuropathy pain, postherpetic neuralgia, trigeminal neuralgia, HIV-polyneuropathy pain, and therapeutic drugs effective against these pains are also expected to be developed.

Capsaicin; (E)-8-methyl-N-vanillyl-6-nonenamide is contained in the juice of plants belonging to the genus *Capsicum*, and is not only used as spices but also known to have analgesic effect and anti-inflammatory effect. Also, civamide, a geometrical isomer of capsaicin; (Z)-8-methyl-N-vanillyl-6-nonenamide is also known to have an analgesic effect. Capsaicin expresses the analgesic effect and anti-inflammatory effect by specifically acting on the particular receptor present in the primary afferent sensory nerve (chiefly C fiber: capsaicin sensitive nerve) but is also known to have intense pungency (pain). Recently, this receptor was cloned and named as vanilloid receptor sub-type 1 (VR1) [Non Patent Literature 1]. Thereafter, the receptor was classified as TRPV in the TRP (transient receptor potential) super family and is called TRPV1 [Non Patent Literature 2].

TRPV1, based on the amino acid sequence thereof, is thought to be a highly $Ca^{2+}$ permeable cation channel having 6 transmembrane domains, and is activated by not only a capsaicin-like compound but also stimulations such as heat or acids, suggesting the possibility of the association with pains caused by various pathological conditions. When capsaicin acts on TRPV1 on the primary afferent sensory nerve, the cation channel of TRPV1 opens, a membrane is depolarized, neuropeptide such as substance P is released, etc. whereby pain is caused. The reason why capsaicin, such a pain stimulant, is practically used for treating pains of such as diabetic neuropathy, rheumatoid arthritis, or the like, is understood that the sensory nerve becomes unresponsive (desensitization) to pain stimulation as a result of the continuous TRPV1 cation channel opening by capsaicin [Non Patent Literature 3].

Under such circumstances, a capsaicin-like compound (TRPV1 agonist) is considered to express an analgesic effect based on the pharmacological mechanism (desensitization of capsaicin sensitive sensory nerve) totally different from that of the existing analgesics, and the effectiveness thereof as a therapeutic drug for various pathological pain conditions such as neuropathic pain to begin with, rheumatoid arthritis, and osteoarthritis, against which the existing analgesics do not work sufficiently, is highly anticipated.

In the U.S., capsaicin is sold as an analgesic in the form of cream. However, this cream has the problem of causing intense painful pungency after initial application. For this reason, it is demanded to develop a compound having the capsaicin-like pharmacological mechanism and sufficient analgesic effect with low pungency as a therapeutic drug against pains caused by various pathological conditions, in particular, such as neuropathic pain, rheumatoid arthritis, and osteoarthritis.

Further, the compound having the capsaicin-like pharmacological mechanism is considered to be also useful as a therapeutic drug for pruritus, allergic and non-allergic rhinitis, overactive bladder, stroke, irritable bowel syndrome, asthma/chronic obstructive pulmonary disease and like respiratory diseases, dermatitis, mucositis, gastroduodenal ulcer and inflammatory bowel syndrome which are the pathological conditions associated with the primary afferent sensory nerve (C fiber).

Furthermore, since it is reported that capsaicin promotes adrenaline secretion and exhibits antiobesity effect [Non Patent Literature 4], the compound having the capsaicin like pharmacological mechanism is considered to be useful as a therapeutic drug against obesity. Still furthermore, since it is reported that the insulin tolerance of a diabetic rat is alleviated by the treatment of capsaicin [Non Patent Literature 5], the compound is thought to be also useful as a therapeutic drug for diabetes.

Citation List

Non Patent Literature

Non Patent Literature 1: Nature, 389, 816 (1997)

Non Patent Literature 2: Annu. Rev. Neurosci., 24, 487 (2001)

Non Patent Literature 3: Pharmacol. Rev., 51, 159 (1999)

Non Patent Literature 4: Pharmacol. Rev., 38, 179 (1986)

Non Patent Literature 5: Eur. J. Endocrinol., 153, 963, (2005)

SUMMARY OF INVENTION

Technical Problem

An object of the present invention is to provide a compound useful as a therapeutic drug or a preventive drug against pains and inflammation caused by various pathological conditions such as neuropathic pain, rheumatoid arthritis, and osteoarthritis, and having sufficient analgesic effect with low pungency.

Solution to Problem

The present inventors conducted extensive studies and found that a cyclic amine-1-carboxylic acid ester derivative having a 3,4-disubstituted benzyl carbamoyl group on the cycle, more specifically, the compound represented by the following formula (I) has a strong analgesic effect but a low pungency, whereby the present invention was accomplished. More specifically, the present invention provides the following inventions.

Item 1: A compound represented by the following formula (I):

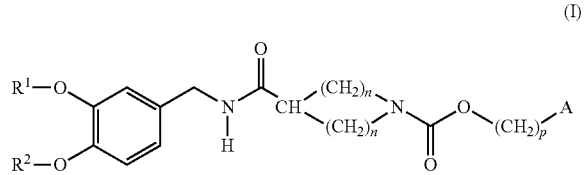

[wherein $R^1$ represents a methyl group or a hydrogen atom, $R^2$ represents a hydrogen atom, a $C_{1-4}$ alkyl group, a $C_{1-4}$ alkylcarbonyl group or an arylcarbonyl group, A represents a $C_{3-8}$ cycloalkyl group, a $C_{3-8}$ cycloalkenyl group, an aryl group or a heteroaryl group (each group may be substituted with 1 to 5 same or different substituents selected from the group consisting of $C_{1-6}$ alkyl, $C_{2-6}$ alkenyl, $C_{3-8}$ cycloalkyl and halogen), n and m, the same or different, each represent an integer of 1, 2 or 3, p represents an integer of 0, 1, 2 or 3]

or a physiologically acceptable salt thereof.

Item 2: The compound according to item 1 wherein, in the formula (I), A represents a $C_{3-8}$ cycloalkyl group or an aryl group (each group may be substituted with 1 to 5 same or different substituents selected from the group consisting of $C_{1-6}$ alkyl, $C_{2-6}$ alkenyl, $C_{3-8}$ cycloalkyl and halogen,) or a physiologically acceptable salt thereof.

Item 3: The compound according to item 1 wherein, in the formula (I), A represents a $C_{3-8}$ cycloalkyl group or an aryl group (each group may be substituted with 1 to 5 same or different substituents selected from the group consisting of $C_{1-6}$ alkyl, $C_{2-6}$ alkenyl and $C_{3-8}$ cycloalkyl,) or a physiologically acceptable salt thereof.

Item 4: The compound according to item 1 wherein, in the formula (I), A represents a $C_{3-8}$ cycloalkyl group (each group may be substituted with 1 to 5 same or different substituents selected from the group consisting of $C_{1-6}$ alkyl, $C_{2-6}$ alkenyl and $C_{3-8}$ cycloalkyl,) or a physiologically acceptable salt thereof.

Item 5: The compound according to any one of items 1 to 4 wherein, in the formula (I), n and m, the same or different, each represent an integer of 1 or 2, or a physiologically acceptable salt thereof.

Item 6: The compound according to any one of items 1 to 4 wherein, in the formula (I), n and m are both 2, or a physiologically acceptable salt thereof.

Item 7: The compound according to any one of items 1 to 6 wherein, in the formula (I), p represents an integer of 0 or 1, or a physiologically acceptable salt thereof.

Item 8: The compound according to any one of items 1 to 6 wherein, in the formula (I), p represents an integer of 0, or a physiologically acceptable salt thereof.

Item 9: The compound according to any one of items 1 to 8 wherein, in the formula (I), $R^1$ is a methyl group, or a physiologically acceptable salt thereof.

Item 10: The compound according to any one of items 1 to 9 wherein, in the formula (I), $R^2$ is a hydrogen atom, or a physiologically acceptable salt thereof.

Item 11: The compound according to item 1 represented by the formula (I) selected from the group consisting of 4-ethylcyclohexyl 4-(4-hydroxy-3-methoxybenzylcarbamoyl)-piperidine-1-carboxylate, 4,4-dimethylcyclohexyl 4-(4-hydroxy-3-methoxybenzylcarbamoyl)-piperidine-1-carboxylate, 3-methylcyclohexyl 4-(4-hydroxy-3-methoxybenzylcarbamoyl)-piperidine-1-carboxylate, 2-methylcyclohexyl 4-(4-hydroxy-3-methoxybenzylcarbamoyl)-piperidine-1-carboxylate, 4,4-dimethylcyclohexyl 3-(4-hydroxy-3-methoxybenzylcarbamoyl)-azetidine-1-carboxylate, 4-t-butylcyclohexyl 3-(4-hydroxy-3-methoxybenzylcarbamoyl)-azetidine-1-carboxylate, 4-t-butylcyclohexyl 3-(4-hydroxy-3-methoxybenzylcarbamoyl)-pyrrolidine-1-carboxylate, 4-methylcyclohexyl 4-(4-hydroxy-3-methoxybenzylcarbamoyl)-piperidine-1-carboxylate, 3,3,5,5-tetramethylcyclohexyl 3-(4-hydroxy-3-methoxybenzylcarbamoyl)-azetidine-1-carboxylate, 2-isopropyl-5-methylcyclohexyl 3-(4-hydroxy-3-methoxybenzylcarbamoyl)-azetidine-1-carboxylate, 4-ethylcyclohexyl 3-(4-hydroxy-3-methoxybenzylcarbamoyl)-pyrrolidine-1-carboxylate, 4,4-dimethylcyclohexyl 3-(4-hydroxy-3-methoxybenzylcarbamoyl)-pyrrolidine-1-carboxylate, 4,4-diethylcyclohexyl 3-(4-hydroxy-3-methoxybenzylcarbamoyl)-pyrrolidine-1-carboxylate, 4-t-butylcyclohexyl 4-(4-hydroxy-3-methoxybenzylcarbamoyl)-piperidine-1-carboxylate, 4-butylcyclohexyl 3-(4-hydroxy-3-methoxybenzylcarbamoyl)-azetidine-1-carboxylate, 4,4-diethylcyclohexyl 4-(4-hydroxy-3-methoxybenzylcarbamoyl)-piperidine-1-carboxylate, 3,5-dimethylcyclohexyl 4-(4-hydroxy-3-methoxybenzylcarbamoyl)-piperidine-1-carboxylate, 2-ethylcyclohexyl 4-(4-hydroxy-3-methoxybenzylcarbamoyl)-piperidine-1-carboxylate, 4-ethylcyclohexyl 3-(4-hydroxy-3-methoxybenzylcarbamoyl)-azetidine-1-carboxylate, 3-ethylcyclohexyl 3-(4-hydroxy-3-methoxybenzylcarbamoyl)-azetidine-1-carboxylate, 4-isopropylcyclohexyl 3-(4-hydroxy-3-methoxybenzylcarbamoyl)-azetidine-1-carboxylate, 2-isopropenyl-5-methylcyclohexyl 3-(4-hydroxy-3-methoxybenzylcarbamoyl)-azetidine-1-carboxylate, cycloheptyl 4-(4-hydroxy-3-methoxybenzylcarbamoyl)-piperidine-1-carboxylate, cyclohexylmethyl 4-(4-hydroxy-3-methoxybenzylcarbamoyl)-piperidine-1-carboxylate, 2-isopropylphenyl 4-(4-hydroxy-3-methoxybenzylcarbamoyl)-piperidine-1-carboxylate, 2-cyclopentylphenyl 4-(4-hydroxy-3-methoxybenzylcarbamoyl)-piperidine-1-carboxylate, 3-isopropylphenyl 4-(4-hydroxy-3-methoxybenzylcarbamoyl)-piperidine-1-carboxylate, 4-isopropylphenyl 4-(4-hydroxy-3-methoxybenzylcarbamoyl)-piperidine-1-carboxylate, 2-isopropylphenyl 3-(4-hydroxy-3-methoxybenzylcarbamoyl)-azetidine-1-carboxylate, 2-cyclopentylphenyl 3-(4-hydroxy-3-methoxybenzylcarbamoyl)-azetidine-1-carboxylate, and cyclohexyl 4-(4-hydroxy-3-methoxybenzylcarbamoyl)-piperidine-1-carboxylate, or a physiologically acceptable salt thereof.

Item 12: The compound according to item 1 represented by the formula (I) selected from the group consisting of 4-ethylcyclohexyl 4-(4-hydroxy-3-methoxybenzylcarbamoyl)-piperidine-1-carboxylate, 4,4-dimethylcyclohexyl 4-(4-hydroxy-3-methoxybenzylcarbamoyl)-piperidine-1-carboxylate, 3-methylcyclohexyl 4-(4-hydroxy-3-methoxybenzylcarbamoyl)-piperidine-1-carboxylate,
2-methylcyclohexyl 4-(4-hydroxy-3-methoxybenzylcarbamoyl)-piperidine-1-carboxylate,
4,4-diethylcyclohexyl 3-(4-hydroxy-3-methoxybenzylcarbamoyl)-azetidine-1-carboxylate,
4-t-butylcyclohexyl 3-(4-hydroxy-3-methoxybenzylcarbamoyl)-azetidine-1-carboxylate,
4-t-butylcyclohexyl 3-(4-hydroxy-3-methoxybenzylcarbamoyl)-pyrrolidine-1-carboxylate,
4-methylcyclohexyl 4-(4-hydroxy-3-methoxybenzylcarbamoyl)-piperidine-1-carboxylate,
3,3,5,5-tetramethylcyclohexyl 3-(4-hydroxy-3-methoxybenzylcarbamoyl)-azetidine-1-carboxylate,
2-isopropyl-5-methylcyclohexyl 3-(4-hydroxy-3-methoxybenzylcarbamoyl)-azetidine-1-carboxylate,
4-ethylcyclohexyl 3-(4-hydroxy-3-methoxybenzylcarbamoyl)-pyrrolidine-1-carboxylate,
4,4-dimethylcyclohexyl 3-(4-hydroxy-3-methoxybenzylcarbamoyl)-pyrrolidine-1-carboxylate, and
4,4-diethylcyclohexyl 3-(4-hydroxy-3-methoxybenzylcarbamoyl)-pyrrolidine-1-carboxylate, or a physiologically acceptable salt thereof.

Item 13: The compound according to item 1 represented by the formula (I) selected from the group consisting of
cis-4-ethylcyclohexyl 4-(4-hydroxy-3-methoxybenzylcarbamoyl)-piperidine-1-carboxylate,
trans-4-ethylcyclohexyl 4-(4-hydroxy-3-methoxybenzylcarbamoyl)-piperidine-1-carboxylate,
4,4-dimethylcyclohexyl 4-(4-hydroxy-3-methoxybenzylcarbamoyl)-piperidine-1-carboxylate,
trans-3-ethylcyclohexyl 4-(4-hydroxy-3-methoxybenzylcarbamoyl)-piperidine-1-carboxylate,
cis-2-methylcyclohexyl 4-(4-hydroxy-3-methoxybenzylcarbamoyl)-piperidine-1-carboxylate,
4,4-diethylcyclohexyl 3-(4-hydroxy-3-methoxybenzylcarbamoyl)-azetidine-1-carboxylate,
cis-4-t-butylcyclohexyl 3-(4-hydroxy-3-methoxybenzylcarbamoyl)-azetidine-1-carboxylate,
cis-4-t-butylcyclohexyl (S)-3-(4-hydroxy-3-methoxybenzylcarbamoyl)-pyrrolidine-1-carboxylate, cis-4-methylcyclohexyl 4-(4-hydroxy-3-methoxybenzylcarbamoyl)-piperidine-1-carboxylate,
3,3,5,5-tetramethylcyclohexyl 3-(4-hydroxy-3-methoxybenzylcarbamoyl)-azetidine-1-carboxylate,
(1S,2S,5R)-2-isopropyl-5-methylcyclohexyl 3-(4-hydroxy-3-methoxybenzylcarbamoyl)-azetidine-1-carboxylate,
cis-4-ethylcyclohexyl (S)-3-(4-hydroxy-3-methoxybenzylcarbamoyl)-pyrrolidine-1-carboxylate, 4,4-dimethylcyclohexyl (S)-3-(4-hydroxy-3-methoxybenzylcarbamoyl)-pyrrolidine-1-carboxylate, and
4,4-diethylcyclohexyl (S)-3-(4-hydroxy-3-methoxybenzylcarbamoyl)-pyrrolidine-1-carboxylate, or a physiologically acceptable salt thereof.

Item 14: The compound according to item 1 represented by the formula (I) selected from the group consisting of
cis-4-ethylcyclohexyl 4-(4-hydroxy-3-methoxybenzylcarbamoyl)-piperidine-1-carboxylate,
trans-4-ethylcyclohexyl 4-(4-hydroxy-3-methoxybenzylcarbamoyl)-piperidine-1-carboxylate,
4,4-dimethylcyclohexyl 4-(4-hydroxy-3-methoxybenzylcarbamoyl)-piperidine-1-carboxylate,
trans-3-ethylcyclohexyl 4-(4-hydroxy-3-methoxybenzylcarbamoyl)-piperidine-1-carboxylate,
cis-2-methylcyclohexyl 4-(4-hydroxy-3-methoxybenzylcarbamoyl)-piperidine-1-carboxylate,
4,4-diethylcyclohexyl 3-(4-hydroxy-3-methoxybenzylcarbamoyl)-azetidine-1-carboxylate,
cis-4-t-butylcyclohexyl 3-(4-hydroxy-3-methoxybenzylcarbamoyl)-azetidine-1-carboxylate,
cis-4-t-butylcyclohexyl (S)-3-(4-hydroxy-3-methoxybenzylcarbamoyl)-pyrrolidine-1-carboxylate, cis-4-methylcyclohexyl 4-(4-hydroxy-3-methoxybenzylcarbamoyl)-piperidine-1-carboxylate,
trans-4-methylcyclohexyl 4-(4-hydroxy-3-methoxybenzylcarbamoyl)-piperidine-1-carboxylate,
cis-4-t-butylcyclohexyl 4-(4-hydroxy-3-methoxybenzylcarbamoyl)-piperidine-1-carboxylate,
cycloheptyl 4-(4-hydroxy-3-methoxybenzylcarbamoyl)-piperidine-1-carboxylate,
cyclohexylmethyl 4-(4-hydroxy-3-methoxybenzylcarbamoyl)-piperidine-1-carboxylate,
cis-3-methylcyclohexyl 4-(4-hydroxy-3-methoxybenzylcarbamoyl)-piperidine-1-carboxylate,
trans-2-ethylcyclohexyl 4-(4-hydroxy-3-methoxybenzylcarbamoyl)-piperidine-1-carboxylate,
trans-4-t-butylcyclohexyl 3-(4-hydroxy-3-methoxybenzylcarbamoyl)-azetidine-1-carboxylate,
3,3,5,5-tetramethylcyclohexyl 3-(4-hydroxy-3-methoxybenzylcarbamoyl)-azetidine-1-carboxylate,
cis-4-t-butylcyclohexyl 3-(4-hydroxy-3-methoxybenzylcarbamoyl)-azetidine-1-carboxylate,
cyclohexyl 4-(4-hydroxy-3-methoxybenzylcarbamoyl)-piperidine-1-carboxylate, or a physiologically acceptable salt thereof.

Item 15: The compound according to item 1 represented by the formula (I) selected from the group consisting of
cis-4-ethylcyclohexyl 4-(4-hydroxy-3-methoxybenzylcarbamoyl)-piperidine-1-carboxylate,
trans-4-ethylcyclohexyl 4-(4-hydroxy-3-methoxybenzylcarbamoyl)-piperidine-1-carboxylate,
4,4-dimethylcyclohexyl 4-(4-hydroxy-3-methoxybenzylcarbamoyl)-piperidine-1-carboxylate,
trans-3-methylcyclohexyl 4-(4-hydroxy-3-methoxybenzylcarbamoyl)-piperidine-1-carboxylate,
cis-2-methylcyclohexyl 4-(4-hydroxy-3-methoxybenzylcarbamoyl)-piperidine-1-carboxylate,
4,4-diethylcyclohexyl 3-(4-hydroxy-3-methoxybenzylcarbamoyl)-azetidine-1-carboxylate,
cis-4-t-butylcyclohexyl 3-(4-hydroxy-3-methoxybenzylcarbamoyl)-azetidine-1-carboxylate, and
cis-4-t-butylcyclohexyl (S)-3-(4-hydroxy-3-methoxybenzylcarbamoyl)-pyrrolidine-1-carboxylate, or a physiologically acceptable salt thereof.

Item 16: A pharmaceutical composition containing the compound according to any one of claims 1 to 15 or the physiologically acceptable salt thereof as an active ingredient.

Item 17: A therapeutic agent or a preventive agent for pain and/or inflammation containing the compound according to any one of items 1 to 15 or the physiologically acceptable salt thereof as an effective ingredient.

Item 18: An analgesic or anti-inflammatory drug containing the compound according to any one of items 1 to 15 or the physiologically acceptable salt thereof as an effective ingredient.

Item 19: A method for treating or preventing pain and/or inflammation including administrating to a patient an effective amount of the compound according to any one of items 1 to 15 or the physiologically acceptable salt thereof.

Item 20: A method for treating pain and/or inflammation comprising administrating to a patient who requires treatment or prevention of pains and/or inflammation an effective amount of the compound according to any one of items 1 to 15 or the physiologically acceptable salt thereof.

Item 21: Use of the compound according to any one of items 1 to 15 or the physiologically acceptable salt thereof for producing a therapeutic agent or a preventive agent for pain and/or inflammation.

Item 22: Use of the compound according to any one of items 1 to 15 or the physiologically acceptable salt thereof for producing a pharmaceutical for treating or preventing pain and/or inflammation.

Item 23: A pharmaceutical comprising the compound according to any one of items 1 to 15 or the physiologically acceptable salt thereof and at least one other drug selected from the group consisting of a narcotic analgesic, a neuropathic pain therapeutic agent, a non-steroidal anti-inflammatory drug, a steroidal anti-inflammatory drug, an antidepressant, an antiepileptic drug, an antispasmogenic, an anesthetic, an antiarrhythmic drug, a local anesthetic and an anti-anxiety drug.

Item 24: A pharmaceutical composition containing the pharmaceutical according to item 23 as an active ingredient.

Item 25: A therapeutic agent or a preventive agent for pain and/or inflammation containing the pharmaceutical according to item 23 as an effective ingredient.

Item 26: A method for treating or preventing pain and/or inflammation including administering to a patient who requires treatment or prevention of pain and/or inflammation an effective amount of the pharmaceutical according to item 23.

Item 27: Use of the pharmaceutical according to item 23 for producing a therapeutic agent or a preventive agent for pain and/or inflammation.

Advantageous Effects of Invention

According to the present invention, since a compound having a strong analgesic effect with low pungency can be provided, an analgesic and anti-inflammatory drug, for example, a therapeutic agent or a preventive agent for pains and/or inflammation caused by neuropathic pain, inflammatory pain, musculoskeletal pain, visceral pain, bone pain, cancer pain and the combination of these pains and/or inflammation against which the existing analgesics do not sufficiently work can be provided. Examples of the pathological conditions which cause the pain and/or inflammation include a variety of neuropathic pains such as, to begin with, diabetic neuropathy pain, postherpetic neuralgia, trigeminal neuralgia, HIV-polyneuropathy pain, postoperative pain, central and peripheral neuropathy and neuropathic low back pain, rheumatoid arthritis, osteoarthritis, low back pain, fibromyalgia syndrome, atypical chest pain, herpes neuralgia, phantom limb pain, pelvic pain, fascial facial pain, abdominal pain, neck pain, central pain, toothache, opioid tolerant pain, visceral pain, operative pain, bone damage pain, angina pectoris pain and other pains/inflammation which require treatment.

Further, according to the present invention, a therapeutic agent or a preventive agent can be provided for migraine headache or cluster headache, pruritus, allergic or non-allergic rhinitis, overactive bladder, stroke, irritable bowel syndrome, respiratory diseases such as asthma/chronic obstructive pulmonary disease, dermatitis, mucositis, gastroduodenal ulcer, inflammatory bowel syndrome, and diabetes, obesity.

DESCRIPTION OF EMBODIMENTS

Hereinafter, the compound represented by the formula (I) of the present invention is further described.

The physiologically acceptable salt of the compound represented by the formula (I) means a physiologically acceptable acid adduct salt of the compound of the formula (I) containing a group capable of forming an acid adduct salt in the structure, or a salt formed with a physiologically acceptable base of the compound of the formula (I) containing a group capable of forming a salt with the base in the structure. Specific examples of the acid adduct salt include inorganic acid salts such as hydrochloride, hydrobromate, hydroiodic acid salt, sulfate, perchlorate, and phosphate, organic acid salts such as oxalate, malonate, maleate, fumarate, lactate, malate, citrate, tartrate, benzoate, trifluoroacetic acid salt, acetate, methanesulfonic acid salt, p-toluenesulfonic acid salt, and trifluoromethanesulfonic acid salt, as well as amino acids such as glutamate and aspartic acid salt. Specific examples of the salt formed with a base include alkali metals or alkali earth metal salts such as sodium salt, potassium salt or calcium salt, salts with an organic base such as pyridine salt and triethylamine salt, and salts with an amino acid such as lysine or arginine.

Since the compounds of the formula (I) and salts thereof may present in the form of a hydrate and/or a solvate, the hydrates and/or solvates thereof are also encompassed as the compound of the present invention. More specifically, "the compound of the present invention" encompasses, in addition to the compounds represented by the above formula (I) and physiologically acceptable salts thereof, the hydrates and/or solvates thereof.

Further, since the compound of the formula (I) sometimes has the case wherein one or more asymmetric carbon atoms or sometimes causes geometrical isomerism and axial chirality, the compound can be present in several different stereoisomers. In the present invention, these stereoisomers, mixtures thereof and racemic compounds thereof are encompassed in the compound represented by the formula (I).

The terms used in this specification are described below.

The "alkyl group" means a linear or branched saturated hydrocarbon group, and, for example, the "$C_{1-4}$ alkyl group" or "$C_{1-6}$ alkyl" means a group having 1 to 4 or 1 to 6 carbon atoms. Specific examples include methyl, ethyl, propyl, isopropyl, butyl, isobutyl, sec-butyl, tert-butyl etc. as the "$C_{1-4}$ alkyl group", and pentyl, isopentyl, neopentyl, hexyl etc. in addition to the above as the "$C_{1-6}$ alkyl". Such alkyl groups may be linear. Alternatively, they may be branched.

The "alkenyl group" means a linear or branched unsaturated hydrocarbon group having at least one double bond. For example, the "$C_{2-6}$ alkenyl" means an unsaturated hydrocarbon group of 2 to 6 carbon atoms having at least one double bond. Specific examples thereof include vinyl, allyl, 1-propenyl, isopropenyl, 1-, 2- or 3-butenyl, 1,3-butadienyl, 2-, 3- or 4-pentenyl, 2-methyl-2-butenyl, 3-methyl-1-butenyl, 3-methyl-2-butenyl, 4-methyl-1-pentenyl, 3,3-dimethyl-1-butenyl and 5-hexenyl etc. Such an alkenyl group may be linear. Alternatively, it may be branched. Moreover, the number of the double bond which the alkenyl group contains may be one. Alternatively, the number may be two.

The "$C_{3-8}$ cycloalkyl group" means a monocyclic saturated hydrocarbon group having 3 to 8 carbon atoms. Specific examples thereof include cyclopropyl, cyclobutyl, cyclopentyl, cyclohexyl, cycloheptyl and cyclooctyl.

The "$C_{3-8}$ cycloalkenyl group" means a monocyclic unsaturated hydrocarbon group containing one or two double bonds having 3 to 8 carbon atoms. Specific examples thereof include a cyclohexenyl group, a cycloheptenyl group, a cyclopentenyl group and a 2,4-cyclohexadienyl group etc. The number of the double bond which the cycloalkenyl group contains is preferably one.

The "aryl group" means phenyl or naphthyl, and phenyl is preferable. Similarly, the "aryl carbonyl group" means phenyl carbonyl or naphthyl carbonyl.

The "heteroaryl group" means a 1 to 3 cyclic unsaturated heterocyclic group comprising 1 to 4 hetero atoms selected from the group consisting of a nitrogen atom, an oxygen atom and a sulfur atom as well as 1 to 12 carbon atoms wherein each ring is a 3 to 8 membered ring. Specific examples thereof include thienyl, furyl, pyranyl, pyrrolyl, imidazolyl, pyridyl, pyrazinyl, isoxazolyl, pyrazolyl, isothiazolyl, pyrimidinyl, oxadiazolyl, thiadiazolyl, benzoisoxazolyl, benzoxadiazolyl, benzothiadiazolyl, pyridazinyl, pyrazolopyridinyl, cinnolinyl, triazolyl, quinolyl, isoquinolyl and naphthyridinyl. Examples of the "halogen" include fluorine, chlorine, bromine and iodine.

The number of the carbon atoms in the "$C_{1-4}$ alkylcarbonyl" modifies only the group or moiety which follows immediately thereafter. Accordingly, in the above case, $C_{1-4}$ modifies only the alkyl and the "$C^1$ alkylcarbonyl" corresponds to acetyl. Thus, specific examples of the "$C_{1-4}$ alkylcarbonyl group" include acetyl, propionyl, propylcarbonyl, isopropylcarbonyl, butylcarbonyl, isobutylcarbonyl and tert-butylcarbonyl etc.

The "cycloalkyl group substituted with alkyl" means those wherein 1 or more (e.g., 1 to 5, preferably 1 to 4) hydrogen atoms of the above cycloalkyl group are substituted with the above alkyl. Specific examples include 2-methylcyclohexyl, 3-methylcyclohexyl, 4-methylcyclohexyl, 2-ethylcyclohexyl, 3-ethylcyclohexyl, 4-ethylcyclohexyl, 4,4-dimethylcyclohexyl, 3,5-dimethylcyclohexyl, 3,3,5,5-tetramethylcyclohexyl, 4,4-diethylcyclohexyl, 2-isopropyl-5-methylcyclohexyl, 4-butylcyclohexyl, 4-propylcyclohexyl, 4-isopropylcyclohexyl and 4-t-butylcyclohexyl. Each of the following substituents substituted with alkyl: a cycloalkenyl group, an aryl group and a heteroaryl group are also the same.

The "cycloalkyl group substituted with alkenyl" means those wherein 1 or more (e.g., 1 to 2, preferably 1) hydrogen atoms of the above cycloalkyl group are substituted with the above alkenyl. Specific examples include 2-ethenylcyclohexyl, 3-ethenylcyclohexyl, 4-ethenylcyclohexyl, 2-(1-propenyl)cyclohexyl, 3-(1-propenyl)cyclohexyl, 4-(1-propenyl)cyclohexyl, 2-isopropenylcyclohexyl, 3-isopropenylcyclohexyl, 4-isopropenylcyclohexyl, 4-(1-butenyl)cyclohexyl, 4-(2-butenyl)cyclohexyl and 4-(1-isobutenyl)cyclohexyl etc. Each of the following substituents substituted with alkenyl: a cycloalkenyl group, an aryl group and a heteroaryl group are also the same.

The "aryl group substituted with cycloalkyl" means those wherein 1 or more (e.g., 1 to 3, preferably 1) hydrogen atoms of the above aryl group are substituted with cycloalkyl. Specific examples include 2-cyclopropylphenyl, 4-cyclopropylphenyl, 2-cyclobutylphenyl, 4-cyclobutylphenyl, 2-cyclopentylphenyl, 4-cyclopentylphenyl, 2-cyclohexylphenyl and 4-cyclohexylphenyl etc. Each of the following substituents substituted with cycloalkyl: a cycloalkyl group, a cycloalkenyl group and a heteroaryl group are also the same.

The "aryl group substituted with halogen" means those wherein 1 or more (e.g., 1 to 5, preferably 1 to 2) hydrogen atoms of the above aryl group are substituted with halogen. Specific examples include 2-fluorophenyl, 4-fluorophenyl, 2-chlorophenyl, 4-chlorophenyl, 2-bromophenyl, 4-bromophenyl, 2-iodophenyl and 4-iodophenyl etc. Each of the following substituents substituted with halogen: a cycloalkyl group, a cycloalkenyl group and a heteroaryl group are also the same.

When the case wherein the hydrogen atom of a cycloalkyl group, a cycloalkenyl group, an aryl group or a heteroaryl group is substituted with a plurality of substituents, these substituents may be the same or different. Specific examples thereof include those wherein the above examples are combined as necessary.

Examples of each group in the compound (I) of the present invention are as follows.

$R^1$ is a methyl group or a hydrogen atom, and preferable is a methyl group. $R^2$ is a hydrogen atom, a $C_{1-4}$ alkyl group, a $C_{1-4}$ alkylcarbonyl group or an aryl carbonyl group, and preferable is a hydrogen atom.

A is a $C_{3-8}$ cycloalkyl group, a $C_{3-8}$ cycloalkenyl group, an aryl group or a heteroaryl group and each group may be substituted at a substitutable position with $C_{1-6}$ alkyl, $C_{2-6}$ alkenyl, $C_{3-8}$ cycloalkyl or halogen and, for example, may be substituted with same or different 1 to 5 such substituents.

The cycloalkyl group is preferably a $C_{4-8}$ cycloalkyl group, more preferably a $C_{5-7}$ cycloalkyl group. Further, the cycloalkyl group is preferably unsubstituted or substituted with 1 to 5 same or different $C_{1-6}$ alkyl, $C_{2-6}$ alkenyl or $C_{3-8}$ cycloalkyl, more preferably unsubstituted or substituted with 1 to 5 same or different $C_{1-4}$ alkyl, $C_{2-4}$ alkenyl or $C_{3-6}$ cycloalkyl.

The cycloalkenyl group is preferably a $C_{4-8}$ cycloalkenyl group, more preferably a $C_{5-8}$ cycloalkenyl group. Further, the cycloalkenyl group may be unsubstituted or substituted at a substitutable position with 1 to 5, preferably 1 to 2, same or different $C_{1-6}$ alkyl, $C_{2-6}$ alkenyl or $C_{3-8}$ cycloalkyl, preferably unsubstituted or substituted with 1 to 2 same or different $C_{1-4}$ alkyl, $C_{2-4}$ alkenyl or $C_{3-6}$ cycloalkyl group.

The aryl group is preferably a phenyl group. Further, the aryl group is preferably unsubstituted or substituted with 1 to 5 same or different $C_{1-6}$ alkyl, $C_{2-6}$ alkenyl or $C_{3-8}$ cycloalkyl, more preferably unsubstituted or substituted with 1 to 2 same or different $C_{1-5}$ alkyl, $C_{2-5}$ alkenyl or $C_{3-6}$ cycloalkyl.

Examples of the heteroaryl group preferably include thienyl, furyl, pyranyl, pyrrolyl, imidazolyl, pyridyl, pyrazinyl, isoxazolyl, pyrazolyl, isothiazolyl, pyrimidinyl, oxadiazolyl, thiadiazolyl, benzoisoxazolyl, benzoxadiazolyl, benzothiadiazolyl, pyridazinyl, pyrazolopyridinyl, cinnolinyl, triazolyl, quinolyl, isoquinolyl and naphthyridinyl etc., and more preferably include thienyl, furyl, pyranyl, pyrrolyl, imidazolyl, pyridyl, pyrazinyl, isoxazolyl, pyrazolyl, isothiazolyl, pyrimidinyl, oxadiazolyl, thiadiazolyl, benzoisoxazolyl, benzoxadiazolyl, benzothiadiazolyl, quinolyl, isoquinolyl and naphthyridinyl. Further, the heteroaryl group is preferably unsubstituted or substituted at a substitutable position with 1 to 5 same or different $C_{1-6}$ alkyl, $C_{2-6}$ alkenyl or $C_{3-8}$ cycloalkyl, more preferably unsubstituted or substituted with 1 to 2 same or different $C_{1-5}$ alkyl, $C_{2-5}$ alkenyl or $C_{3-6}$ cycloalkyl.

Among the A, more preferable group include a $C_{5-7}$ cycloalkyl group which may be substituted with 1 to 4 same or different $C_{1-6}$ alkyl (preferably $C_{1-4}$ alkyl), $C_{2-6}$ alkenyl or $C_{3-8}$ cycloalkyl group, or a phenyl group which may be substituted with 1 to 2 same or different $C_{1-6}$ alkyl or $C_{3-6}$ cycloalkyl group.

The n and m are the same or different and each represents an integer of 1, 2 or 3, preferably 1 or 2, more preferably both represent an integer of 1 or 2, or either one of them represents 1 and the other represents 2. Both of them are especially preferably 2.

More specifically, A is preferably a $C_{5-7}$ cycloalkyl group which may be substituted with 1 to 4 same or different $C_{1-6}$ alkyl (preferably $C_{1-4}$ alkyl) or $C_{2-6}$ alkenyl, and n and m are both preferably 2.

The p represents an integer of 0, 1, 2 or 3, preferably 0, 1 or 2, more preferably 0 or 1. Especially preferable integer is 0.

The preferable compound in the present invention is a compound represented by the following formula (I')

[Chemical Formula 2]

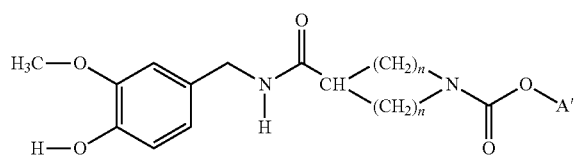

(I')

[wherein A' is a $C_{5-7}$ cycloalkyl group which may be substituted with 1 to 4 same or different $C_{1-6}$ alkyl, $C_{2-6}$ alkenyl or $C_{3-8}$ cycloalkyl, n and m both represent an integer of 1 or 2, or either one of them is 1 and the other is 2], or a physiologically acceptable salt thereof.

In the formula (I'), A' is preferably a $C_{5-7}$ cycloalkyl group (preferably a $C_6$ cycloalkyl group) which may be substituted with 1 to 4 same or different $C_{1-6}$ alkyl (preferably $C_{1-4}$ alkyl) or $C_{2-6}$ alkenyl, and n and m are both 2.

In the present specification, the following abbreviations may sometimes be used to simplify the description.

Me: methyl group, Bu: butyl group, t-: tert-, i-: iso-, s-: sec-, THF: tetrahydrofuran, DMF: N,N-dimethylformamide, TFA: trifluoroacetic acid.

Manufacturing process of the compounds of the invention

The compounds of formula (I) and physiologically acceptable salts thereof are unknown, which can be prepared according to the following processes, the below-mentioned Examples or any processes known in the art.

The compound used in the following processes may be a salt thereof as far as the salt does not disturb the reaction.

Further, in each of the following reactions, when any starting material includes any substituent(s) which may be reactive such as amino group, carboxyl group, hydroxyl group, and carbonyl group; the substituent can be protected by introducing a conventional protective group to the substituent. And the protective group can be optionally removed to give the desired compound.

Examples of the protection group used for an amino group include alkylcarbonyl such as acetyl and propionyl; formyl; phenylcarbonyl; alkyloxycarbonyl such as methoxycarbonyl, ethoxycarbonyl, t-butoxycarbonyl; phenyloxycarbonyl; aralkyloxycarbonyl such as benzyloxycarbonyl; trityl; phthaloyl; and tosyl.

Example of the protection group used for a carboxyl group include alkyl such as methyl, ethyl, propyl, isopropyl, butyl and tert-butyl; phenyl; benzyl; trityl; and silyl.

Examples of the protection group used for a hydroxyl group include methyl; tert-butyl; allyl; substituted methyl such as methoxymethyl and methoxyethoxymethyl; ethoxyethyl; tetrahydropyranyl; tetrahydrofuranyl; trityl; aralkyl such as benzyl; alkylcarbonyl such as acetyl and propionyl; formyl; benzoyl; aralkyloxycarbonyl such as benzyloxycarbonyl; and silyl.

The protection of a carbonyl group is carried out by converting a carbonyl group into acyclic ketal such as dimethyl ketal or diethyl ketal or cyclic ketal such as 1,3-dioxolane or 1,3-dioxane.

Process of the Compound of the Formula (I) (1)

[Chemical Formula 3]

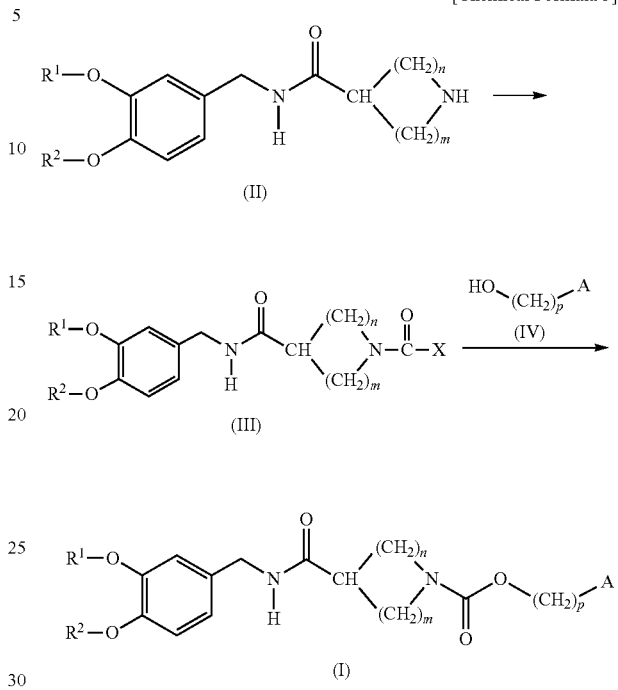

(wherein $R^1$, $R^2$, A, m, n and p are defined as described in item 1, X represents a leaving group (e.g., a halogen atom, a lower alkoxy group, a phenoxy group, an imidazolyl group)

The compound of the formula (I) can be produced by converting the compound of the formula (II) to a reactive derivative represented by the formula (III), which is then reacted to the compound of the formula (IV) under the routinely employed conditions.

The reaction of the compound of the formula (III) with the compound of the formula (IV) described above is typically carried out in a solvent or without a solvent. The solvent used should be selected in accordance with the type or the like of a raw material compound, and examples include toluene, THF, dioxane, ethylene glycol dimethyl ether, methylene chloride, chloroform, ethyl acetate, acetone, acetonitrile, and DMF. Each of these solvents may be used singly, or two or more may be used as a mixed solvent. Also, the reaction is typically used in the presence of a base. Specific examples of the base include inorganic bases such as potassium carbonate and sodium bicarbonate, or organic bases such as triethylamine, ethyl diisopropylamine, N-methyl morpholine, pyridine and 4-dimethylaminopyridine. The reaction temperature varies depending on the type and the like of a raw material compound to be used, but is typically about −30° C. to about 150° C., preferably about −10° C. to about 80° C. The reaction time is about 1 hour to about 48 hours.

The production of the compound (III) from the compound (II) can be carried out by methods described in J. Org. Chem., 27, 961 (1962), J. Chem. Soc., Perkin Trans. 1, 1205 (1996), Tetrahedron, 61, 7153 (2005), etc., or a method in accordance therewith. The compound of the formula (II) may be used in the form of an acid adduct salt such as hydrochloride, and allowed to form a free base in the reaction system.

Process of the Compound of the Formula (I) (2)

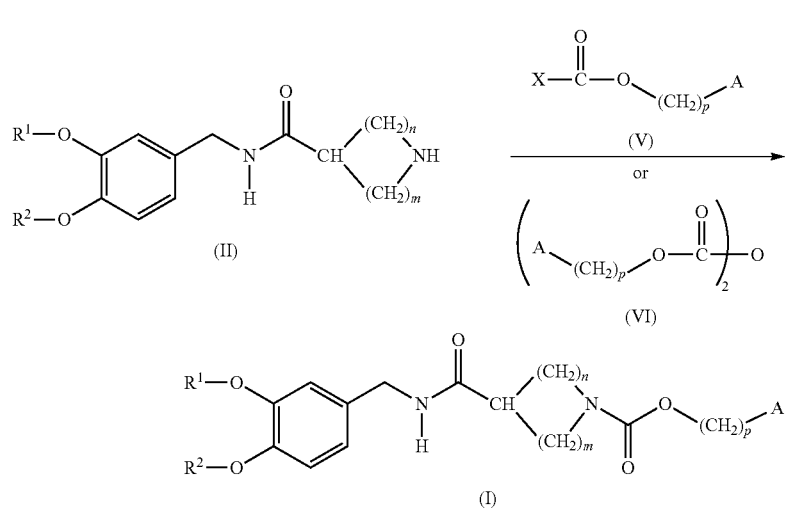

(wherein $R^1$, $R^2$, A, m, n and p are defined as described in item 1, X represents a leaving group (e.g., a halogen atom, a lower alkoxy group, a phenoxy group, an imidazolyl group))

The compound of the formula (I) can be produced by reacting the compound of the formula (II) to the compound of the formula (V) or the formula (VI) under the routinely employed conditions.

The reaction of the compound of the formula (II) with the compound of the formula (V) or (VI) described above is typically carried out in a solvent or without a solvent. The solvent used should be selected in accordance with the type or the like of a raw material compound, and examples include toluene, THF, dioxane, ethylene glycol dimethyl ether, methylene chloride, chloroform, ethyl acetate, acetone, acetonitrile, and DMF. Each of these solvents may be used singly, or two or more may be used as a mixed solvent. The compound of the formula (II) may be used in the form of an acid adduct salt such as hydrochloride, and allowed to form a free base in the reaction system. Also, the reaction is typically used in the presence of a base. Specific examples of the base include inorganic bases such as potassium carbonate and sodium bicarbonate, or organic bases such as triethylamine, ethyl diisopropylamine, N-methyl morpholine, pyridine and 4-dimethylaminopyridine. The reaction temperature varies depending on the type and the like of a raw material compound to be used, but is typically about −30° C. to about 150° C., preferably about −10° C. to about 80° C. The reaction time is about 1 hour to about 48 hours.

The compound of the formula (V) may be commercially available or can be produced by known methods as described in, for example, Synthesis, 103 (1993), J. Org. Chem., 53, 2340 (1988), etc., or by a method in accordance therewith. Similarly, the compound of the formula (VI) can be produced by known methods as described in, for example, J. Org. Chem., 27, 1901 (1962), Org. Synth., VI, 418 (1988), etc., or by a method in accordance therewith.

Process of the Compound of the Formula (I) (3)

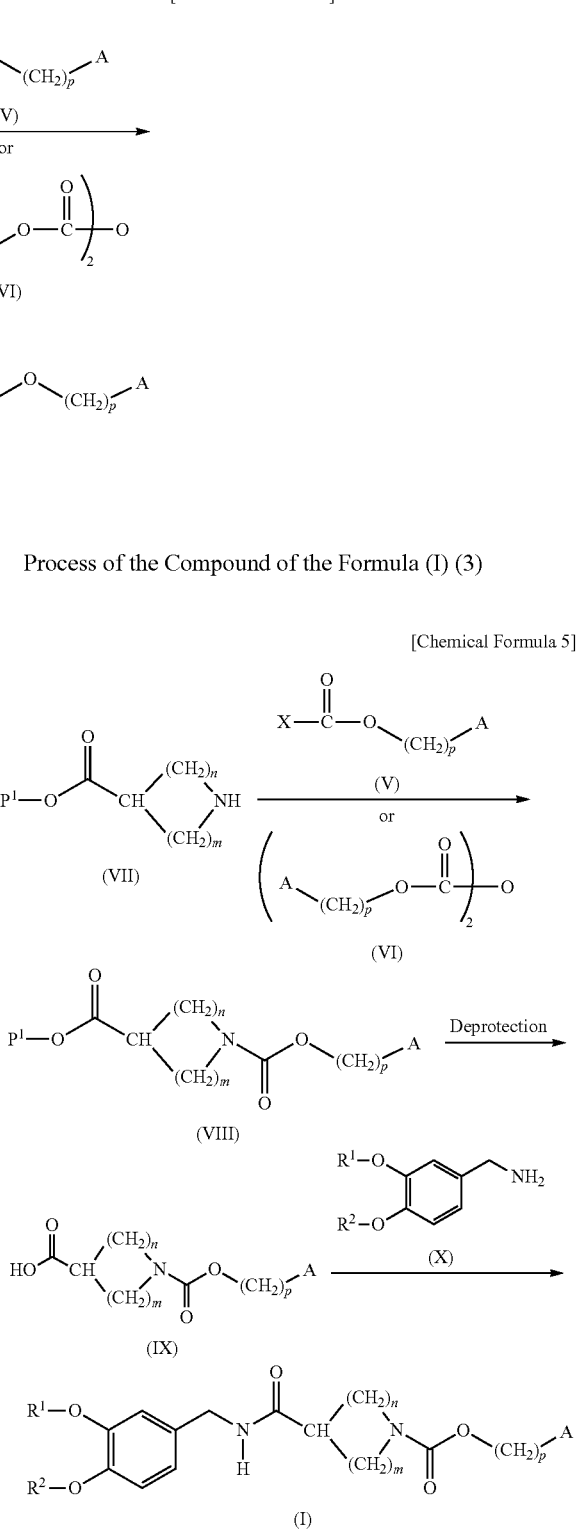

(wherein $R^1$, $R^2$, A, m, n and p are defined as described in item 1, X represents a leaving group (e.g., a halogen atom, a lower alkoxy group, a phenoxy group, an imidazolyl group) and $P^1$ represents the protection group of the carboxy group)

The compound of the formula (I) can be produced by the amidation reaction of the compound of the formula (IX) and the compound of the formula (X) under the routinely employed conditions. The compound of the formula (IX) may be reacted to the compound of the formula (X) after being converted to a reactive derivative in the carboxyl group.

Examples of the reactive derivative of the formula (IX) include lower alkyl ester (particularly methyl ester), active ester, acid anhydride and acid halide (particularly acid chloride). Specific examples of the active ester include p-nitrophenyl ester, N-hydroxysuccinic acid imidoester and pentafluorophenyl ester. Specific example of the acid anhydride include ethyl chlorocarbonate, isobutyl chlorocarbonate, isovaleric acid and a mixed acid anhydride with pivalic acid.

In the reaction, the compound of the formula (IX) may be reacted to the compound of the formula (X) in the presence of a condensation agent. Specific examples of the condensation agent include N,N'-dicyclohexylcarbodiimide, 1-ethyl-3-(3-dimethylaminopropyl)carbodiimide hydrochloride, N,N'-carbonyldiimidazole, and benzotriazol-1-yl-oxytris(pyrrolidino)phosphonium hexafluorophosphate. These condensation agents may be used singly, or in combination with a peptide synthesis reagent such as N-Hydroxysuccinimide or N-hydroxybenzotriazole.

The reaction of the compound of the formula (IX) or a reactive derivative thereof with the compound of the formula (X) described above is typically carried out in a solvent or without a solvent. The solvent used should be selected in accordance with the kind, or the like, of a raw material compound, and examples include toluene, THF, dioxane, ethylene glycol dimethyl ether, methylene chloride, chloroform, ethyl acetate, acetone, acetonitrile, and DMF. Each of these solvents is used singly, or two or more may be used as a mixed solvent. The compound of the formula (X) may be used in the form of an acid adduct salt such as hydrochloride, and allowed to form a free base in the reaction system.

The reaction is typically used in the presence of a base. Specific examples of the base include inorganic bases such as potassium carbonate and sodium bicarbonate as well as organic bases such as triethylamine, ethyl diisopropylamine, N-methyl morpholine, pyridine and 4-dimethylaminopyridine. The reaction temperature varies depending on the type and the like of raw material compounds to be used, but is typically about −30° C. to about 150° C., preferably about −10° C. to about 70° C. The reaction time is about 1 hour to about 48 hours.

The compound of the formula (IX) can be produced by reacting the compound of the formula (VII) to the compound of the formula (V) or the formula (VI) in the same manner as in the above production method (2) to obtain the compound of the formula (VIII), followed by deprotecting the protection group ($P^1$) by a routine method.

Alternatively, the compound of the formula (X) is a known compound or can be produced in accordance a known compound production method. For example, the compound of the formula (X) can be produced by the methods described in Monatsh. Chem., 77, 54 (1947), Tetrahedron Lett., 43, 4281 (2002), J. Org. Chem. and 53, 1064 (1988), J. Org. Chem., 54, 3477 (1989), or a method in accordance therewith. Alternatively, the compound of the formula (VII) is a known compound or can be produced in accordance with a known compound production method.

Process of the Compound of the Formula (II)

[Chemical Formula 6]

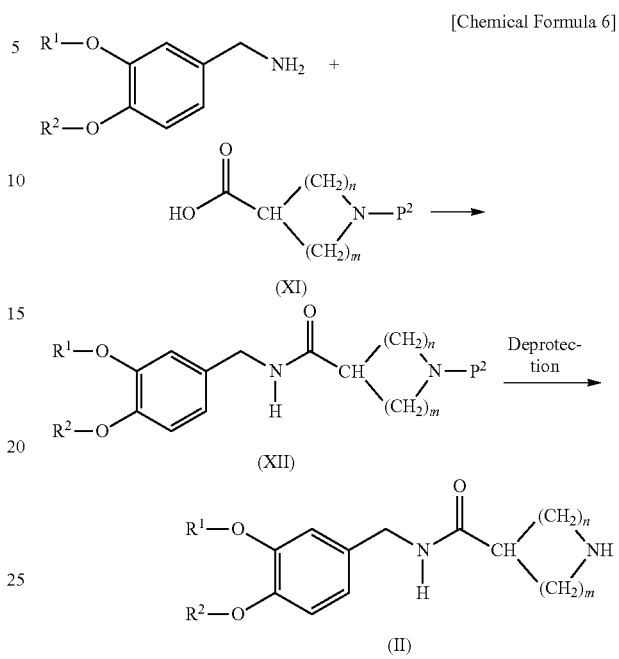

(wherein $R^1$, $R^2$, m and n are defined as described in item 1, and $P^2$ represents a protection group of the amino group)

The compound of the formula (II) can be produced by producing the compound of the formula (XII) using the compound of the formula (X) and the compound of the formula (XI) in the same manner as the amidation reaction in the production method (3) described above, followed by deprotecting the protection group ($P^2$). The compound of the formula (XI) may be reacted to the compound of the formula (X) after being converted to a reactive derivative in the carboxyl group in the same manner as described above.

The compound of the formula (XI) is a known compound or can be produced in accordance with a known compound production method. The production can be carried out by the methods described in, for example, J. Pharm. Sci., 71, 1214 (1982), J. Med. Chem., 31, 613 (1988), or by a method in accordance therewith.

Process of the Compound of the Formula (IV)

The compound of the formula (IV) may be commercially available or can be produced by the known methods as described in, for example, J. Org. Chem., 45, 5399 (1980), J. Chem. Soc., Perkin Trans. 1, 3015 (1999), or by a method in accordance therewith. The representative production methods are described below.

[Chemical Formula 7]

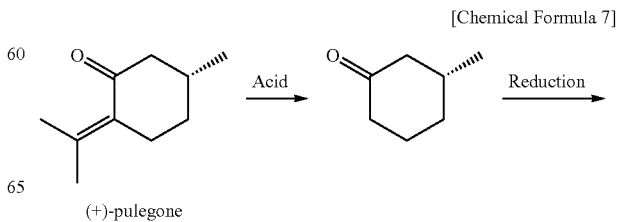

(+)-pulegone

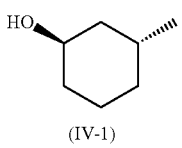

(IV-1)

The production of the compound (IV-1) from (+)-pulegone can be carried out by producing (R)-3-methylcyclohexanone in accordance with the method described in J. Org. Chem., 33, 2647 (1968), which is subsequently subjected to a reduction reaction by the methods described in J. Am. Chem. Soc., 94, 7159 (1972), Tetrahedron Lett., 32, 6243 (1991), etc., using a bulky reducing agent such as lithium tri-sec-butylborohydride.

[Chemical Formula 8]

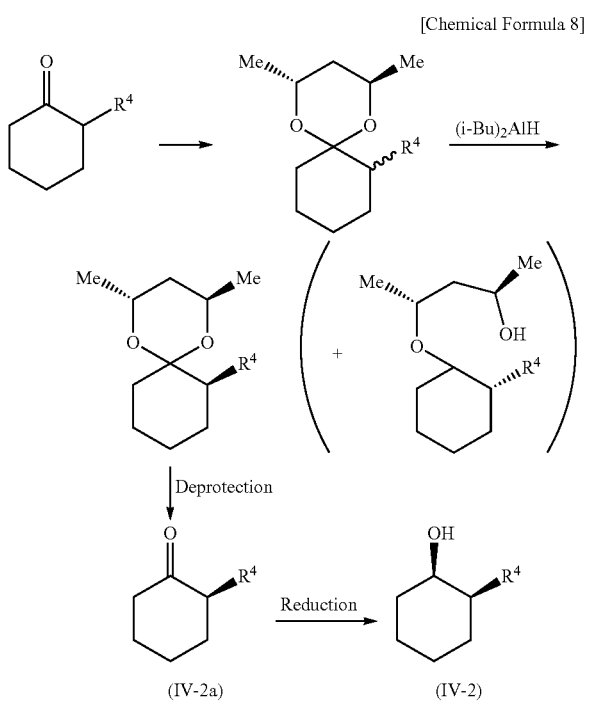

(wherein $R^4$ represents a $C_{1-6}$ alkyl group or a $C_{2-6}$ alkenyl group)

The compound of the formula (IV-2) can be produced by producing (IV-2a) in accordance with the method described in J. Org. Chem., 50, 5444 (1985), which is then treated in accordance with the methods described in J. Am. Chem. Soc., 94, 7159 (1972), Tetrahedron Lett., 32, 6243 (1991), etc. (see the above illustration).

The compound of the formula (I) obtained by the above production methods can be isolated and purified by a routine method such as chromatography, recrystallization and reprecipitation. Further, an optical isomer can be derived from asymmetric synthesis such as using a starting material having an asymmetric center, or can also be derived by using a chiral column or an optical resolution such as fractional crystallization. Geometrical isomers such as cis isomer and trance isomer can possibly be derived synthetically and isolated using a column. The compound of the formula (I) can be obtained in the form of salt in some cases depending on the type of a functional group present in the structural formula, the selection of raw material compounds and the reaction treatment conditions, but can be converted to the compound of the formula (I) in accordance with a routine manner. On the other hand, for example, the compound of the formula (I) having a group capable of forming an acid adduct salt in the structural formula can be led to an acid adduct salt by being treated with various acids in accordance with a routine method.

Since the compounds of the present invention as well as the physiologically acceptable salts thereof and hydrates or solvates thereof exhibit strong analgesic effects but have low pungency, they are effective not only for oral administration but also for parenteral administration such as transdermal, local, transnasal, intravesical-injection administration. Accordingly, the compounds of the present invention, in the form of an analgesic drug and an anti-inflammatory drug, are useful as a therapeutic agent or a preventive agent for pains and/or inflammation caused by neuropathic pain, inflammatory pain, musculoskeletal pain, visceral pain, bone pain, cancer pain and the combination of these pains and/or inflammation, which are not sufficiently treated with the existing analgesics. The compounds are useful as a therapeutic agent or a preventive agent for pains and inflammation caused by pathological conditions such as a variety of neuropathic pains including, to begin with, diabetic neuropathy pain, postherpetic neuralgia, trigeminal neuralgia, HIV-polyneuropathy pain, postoperative pain, central and peripheral neuropathy and neuropathic low back pain, rheumatoid arthritis, osteoarthritis, low back pain, fibromyalgia syndrome, atypical chest pain, herpes neuralgia, phantom limb pain, pelvic pain, fascial facial pain, abdominal pain, neck pain, central pain, toothache, opioid tolerant pain, visceral pain, operative pain, bone damage pain, angina pectoris pain and other pains and inflammation which require treatment. Furthermore, the compounds are also useful as a preventive and/or therapeutic drug for migraine or cluster headache, pruritus, allergic or non-allergic rhinitis, overactive bladder, stroke, irritable bowel syndrome, respiratory diseases such as asthma/chronic obstructive pulmonary disease, dermatitis, mucositis, gastroduodenal ulcer, inflammatory bowel syndrome, diabetes and obesity.

The "neuropathic pain" is a chronic pain caused by a lesion of the peripheral or central nervous system or a pathological change due to such a damage, and could associate with the neuropathic pain or could form the base of the neuropathic pain. Examples of the neuropathic pain are as follows: diabetic neuropathy pain, postherpetic neuralgia, trigeminal neuralgia, post-traumatic pain after amputation (nerve injury factor causing peripheral and/or central sensitization (e.g., phantom limb pain)), neuropathic low back pain, peripheral neuropathy caused by cancers, chemical injuries, toxin, other major surgeries or nerve compression by traumatic injury, radicular pain in low back or cervical region, fibromyalgia, glossopharyngeal neuralgia, reflex sympathetic dystrophy, causalgia, thalamic syndrome, nerve root avulsion, post-thoracotomy pain, or malnutrition, virus or bacterial infection (e.g., herpes zoster or human immunodeficiency virus (HIV)-polyneuropathy pain) or combination thereof, metastatic invasion, adiposis dolorosa, various central and peripheral neuropathies other than listed above, or central pain state associated with thalamus activity, and conditions secondary to the combination thereof are also encompassed in the definition of the neuropathic pain.

The possible administration route of the compound of the present invention is oral or parenteral administration, and percutaneous administration, one of the parenteral administrations, is preferable. The dose of the compound of the present invention varies depending on the kind of the compound, administration form, administration method, symptoms, age, or the like, of a patient, but is generally 0.005 to 150 mg/kg/day, preferably 0.05 to 20 mg/kg/day, which can be administered in one or several portions.

The compound of the present invention can also compose a pharmaceutical in combination with other drugs. Thus, additive and synergistic drug efficacy can be achieved. For example, the compound of the present invention can be used as a pharmaceutical combined with at least one other drug selected from the group consisting of a narcotic analgesic, a neuropathic pain therapeutic agent, a non-steroidal anti-inflammatory drug, a steroidal anti-inflammatory drug, an antidepressant, an antiepileptic drug, an antispasmogenic, an anesthetic, an antiarrhythmic drug, a local anesthetic and an anti-anxiety drug. Among these, at least one other drug is preferably selected from the group consisting of a narcotic analgesic, a neuropathic pain therapeutic drug, a non-steroidal anti-inflammatory drug, an antiepileptic drug, an antiarrhythmic drug and a local anesthetic.

Specific examples of the narcotic analgesics include morphine, codeine, oxycodone, pethidine, fentanyl, pentazocine, tramadol, butorphanol and buprenorphine. Specific examples of the neuropathic pain therapeutic agents include various types such as pregabalin, gabapentin, carbamazepine, lidocaine, duloxetine, and mexiletine. Specific examples of the non-steroidal anti-inflammatory drugs include acetylsalicylic acid, ibuprofen, loxoprofen sodium, diclofenac sodium, acetaminophen, etodolac, meloxicam, celecoxib, and rofecoxib. Specific examples of the steroidal anti-inflammatory drugs include methylprednisolone, prednisolone, and dexamethasone. Specific examples of the antidepressants include amitriptyline, nortriptyline, amoxapine, paroxetine, fluvoxamine, milnacipran, and duloxetine. Specific examples of the antiepileptic drugs include carbamazepine, lamotrigine, gabapentin, and pregabalin. Specific examples of the antispasmogenics include baclofen. Specific examples of the anesthetics include mepivacaine, bupivacaine, tetracaine, dibucaine, and ketamine hydrochloride. Specific examples of the anti-arrhythmic drugs and local anesthetics include lidocaine, procaine, mexiletine, and flecamide. Specific examples of the anti-anxiety drugs include diazepam and etizolam.

Among these, other drugs to be combined with the compound of the present invention are preferably at least one selected from the group consisting of morphine, codeine, fentanyl, pentazocine, carbamazepine, lamotrigine, pregabalin, gabapentin, lidocaine, loxoprofen sodium, diclofenac sodium, acetaminophen, etodolac, meloxicam, celecoxib and rofecoxib.

The pharmaceutical composed of the combination of the compound of the present invention and the above mentioned other drugs can be provided especially as an analgesic and anti-inflammatory drug, for example, as a therapeutic or preventive agent for neuropathic pain, inflammatory pain, musculoskeletal pain, visceral pain, bone pain, cancer pain and the combination of these pains and/or inflammation which are not sufficiently treated with the existing analgesics. Examples of the pathological conditions which cause the pain and/or inflammation include a variety of neuropathic pains such as, to begin with, diabetic neuropathy pain, postherpetic neuralgia, trigeminal neuralgia, HIV-polyneuropathy pain, postoperative pain, central and peripheral neuropathy and neuropathic low back pain, rheumatoid arthritis, osteoarthritis, low back pain, fibromyalgia syndrome, atypical chest pain, herpes neuralgia, phantom limb pain, pelvic pain, fascial facial pain, abdominal pain, neck pain, central pain, toothache, opioid tolerant pain, visceral pain, operative pain, bone damage pain, angina pectoris pain and other pains and inflammation which require treatment. The pharmaceutical composed of the combination of the pharmaceutical compound of the present invention and other drugs can be provided as a therapeutic or preventive agent for pains and/or inflammation of these pathological conditions.

The compound of the present invention or the pharmaceutical composed of combination of the above other drugs therewith is typically administered in the form of a pharmaceutical composition prepared by mixing pharmaceutical carriers therewith. Specific examples include oral agents such as tablets, capsules, granules, powders, syrups, fine granules, liquids, sublingual formulation and suspensions, external preparations such as ointments, suppositories (intrarectal administration agents), intrabladder injection agents, plasters (tapes, transdermal patch preparations, fomentations, etc.), lotions, emulsions, creams, jellies, gels, external use powder, inhalations and nasal drops, injections and drips such as intradermic injections, subcutaneous injections or intravitreal injections including intraperitoneal, intraarticular injections. These pharmaceutical compositions are prepared in accordance with a routine method. More specifically, the compounds represented by the formula (I) or the physiologically acceptable salts thereof can contain pharmaceutical carriers such as excipients, binders, lubricants, stabilizing agents, disintegrants, bases, buffers, solubilizing aids, isotonizing agents, solubilizing aids, pH regulating agents, surfactants, emulsifying agents, suspending agents, dispersing agents, anti-precipitation agents, thickening agents, viscosity regulating agents, gelling agents, soothing agents, preservatives, plasticizers, absorbefacient agents, age resistors, moisturizing agents, antiseptics, and flavoring agents, and two or more pharmaceutical carrier additives may also be selected and used as necessary.

For the pharmaceutical carrier, a substance routinely used in the medical field and unresponsive to the compound of the present invention is used. Specific examples of the pharmaceutical carrier include lactose, cornstarch, white sugar, mannitol, calcium sulfate, crystalline cellulose, croscarmellose sodium, modified starch, carmellose calcium, crospovidone, low substituted hydroxypropylcellulose, methylcellulose, gelatin, gum arabic, ethyl cellulose, hydroxypropylcellulose, povidone, light anhydrous silicic acid, magnesium stearate, talc, sucrose ester of fatty acid, sorbitan esters of fatty acids, hardened oil, carnauba wax, hydroxypropylmethylcellulose, macro goal, cellulose acetate phthalate, hydroxypropylmethylcellulose acetate phthalate, titanium oxide, calcium phosphate, olive oil, purified lanolin, squalane, silicone oil, castor oil, soybean oil, cotton seed oil, liquid paraffin, white vaseline, yellow vaseline, paraffin, lauric acid, myristic acid, oleic acid, stearic acid, lauryl alcohol, myristyl alcohol, oleyl alcohol, cetyl alcohol, beeswax, bleached wax, cholesterol ester, ethylene glycol monoester, propyleneglycol monoester, glyceryl monostearate, isopropyl myristate, isopropyl palmitate, polyethylene glycol, glycerol, propylene glycol, ethanol, sorbitose solution, water, hydrophilic ointment, vanishing cream, absorptive ointment, cold cream, carboxy vinyl polymer, polyvinyl pyrrolidone, polyisobutylene, vinyl acetate copolymer, acrylic copolymer, triethyl citrate, acetyl triethyl citrate, diethyl phthalate, diethyl sebacate, dibutyl sebacate, acetylated monoglyceride, diethylene glycol, dodecylpyrrolidone, urea, ethyl laurate, Eizon, kaolin, bentonite, zinc oxide, agarose, carrageenan, alginic acid or a salt thereof, tragacanth, acacia gum, carboxymethylcellulose, hydroxyethyl cellulose, carboxy vinyl polymer, xanthan gum, dextrin, polyvinyl alcohol, potassium laurate, potassium palmitate, potassium myristate, etc., sodium lauryl sulfate, cetyl sulfate sodium, sulfonated castor oil (turkey red oil), Span (sorbitan stearate, sorbitan monooleate, sorbitan sesquioleate, sorbitan trioleate, etc.), Tween (polysorbate 20, polysorbate 40, polysorbate 60, polysorbate 65, polysorbate 80, polysorbate 85, polyoxyethylene sorbitan fatty acid ester, etc.), polyoxyethylene hydrogenated castor oil (so-called HCO), polyoxyethylene lauryl ether, polyoxyethylene cetyl ether, polyoxyethylene oleyl ether, polyethylene glycol monolaurate, polyethylene glycol monostearate, poloxamer (so called Pluronic), lecithin (including phosphatidylcholine, phosphatidylserine and like refined phospholipids isolated from lecithin) or derivatives thereof such as hydrogenated lecithin, to begin with, fluorocarbon gases (flon-11, flon-12, flon-21, flon-22, flon-113, flon-114, flon-123, flon-142c, flon-134a, flon-227, flon-C318, 1,1,1,2-tetrafluoroethane, etc.), alternative chlorofluorocarbon gases (HFA-227, HFA-134a, etc.), propane, isobutane, butane, diethyl ether, nitrogen gas, carbon dioxide gas, benzalkonium chloride, paraben, sodium phosphate, sodium acetate, sodium chloride, concentrated glycerin, benzalkonium chloride, paraben, salts of stearic acid, starch, and cellulose.

The content of the compound of the present invention in the pharmaceutical composition varies depending on the formulation, but is typically 0.0025 to 20% by weight of the total composition. These pharmaceutical compositions may also contain other therapeutically effective substances.

The pharmaceutical wherein the compound of the present invention is combined with other drugs described above can compose a single pharmaceutical composition containing the compound of the present invention together with other drugs described above. Alternatively, the first pharmaceutical composition containing the compound of the present invention and the second pharmaceutical composition containing other drugs described above are separately provided, and these compositions may separately or simultaneously be given over a certain period of time. More specifically, the pharmaceutical may be a single formulation (combination drug) containing these effective ingredients together, or may be multiple formulations prepared with these effective ingredients separately. When prepared separately, these formulations can be administered individually or simultaneously. Also, when prepared separately, these preparations can be mixed using a diluent before use for simultaneous administration.

In these pharmaceuticals, the mixing ratio of drugs can be suitably selected in accordance with patient's age, sex and weight, symptoms, administration time, dosage form, administration route, drug combination, and the like. The administration route of the pharmaceutical can be oral and parenteral administration.

EXAMPLES

Hereinafter, the present invention is described further specifically with reference to Examples. However, the present invention is not limited to these Examples. The identification of the compounds was carried out using NMR spectrum (300 MHz or 400 MHz), melting point, powder X-ray diffraction, and the like. The R and S in the structural formula both mean a stereochemical absolute configuration on an asymmetric carbon atom, and R* and S* both mean a stereochemical relative configuration on an asymmetric carbon atom. When one substituent and one hydrogen atom are bonded respectively to each one of two positions of the monocycle, the stereochemical relationship of the two substituents are expressed in cis or trans and a hyphen may sometimes be added thereafter to be followed by a compound name.

The measurement of the melting point of the compounds was carried out by differential scanning calorimetric analysis (apparatus: product of TA Instruments, DSC Q1000 model, heating rate: 10° C./min, atmosphere: nitrogen). The values of the melting point given below are melt starting temperatures. The powder X-ray diffraction (XRD) was measured using a Spectris X' Pert Pro (expert) under the conditions of within a diffraction angle range of 2θ4° to 40°, Cu Kα1 ray (wave length 1.54060 angstrom), X-ray tube current 40 milliampere, voltage 45 kilovolt, step 0.01700 degree, and measurement time 101.41770 sec/step. The measurement was carried out using a sample of about 5 milligrams placed on a non-reflective sample holder composed of Si single crystal.

Example 1

Preparation of cis-4-ethylcyclohexyl 4-(4-hydroxy-3-methoxybenzylcarbamoyl)-piperidine-1-carboxylate

[Chemical Formula 9]

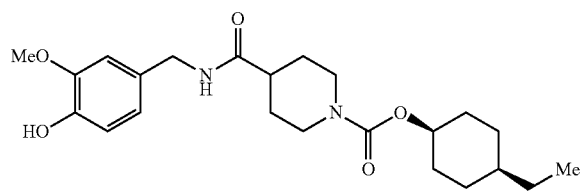 [SMILES: CC[C@H]1CC[C@H](OC(=O)N2CCC(C(=O)NCc3ccc(O)c(OC)c3)CC2)CC1]

(1) 1-Ethyl-3-(3-dimethylaminopropyl)carbodiimide hydrochloride (12.5 g) was added to a mixture of 4-benzyloxy-3-methoxy benzylamine hydrochloride (14.0 g), 1-(t-butoxycarbonyl)-piperidine-4-carboxylic acid (11.5 g), triethylamine (14.0 ml) and methylene chloride (300 ml). After stirring the reaction mixture at room temperature for 20 hours, the mixture was washed with saturated ammonium chloride aqueous solution and then saturated brine, the organic layer was dried over sodium sulfate and the solvent was evaporated under reduced pressure. The residue was purified by silica gel chromatography (elution solvent: hexane/ethyl acetate=100/0 to 0/100 gradient) to obtain 16.3 g of t-butyl-4-(4-benzyloxy-3-methoxybenzylcarbamoyl)-piperidine-1-carboxylate.

(2) The product (16.3 g) of the above (1) was dissolved in ethyl acetate (270 ml) and 4 mol/l hydrogen chloride/ethyl acetate (90 ml) was added thereto. After stirring the mixture for 6 hours, hexane (200 ml) was added to the reaction mixture and the precipitated crystal was filtered to obtain 11.4 g of N-(4-benzyloxy-3-methoxybenzyl)-4-piperidinecarboxamide hydrochloride.

(3) N,N'-carbonyldiimidazole (3.70 g) was added to a mixture of cis-4-ethylcyclohexanol (2.33 g) and methylene chloride (80 ml). After stirring the reaction mixture at room temperature for 20 hours, the mixture was washed with water twice, the organic layer was dried over sodium sulfate and the solvent was evaporated under reduced pressure. The product (4.96 g) of the above (2), triethylamine (14.0 ml), 4-dimethylaminopyridine (120 mg) and DMF (50 ml) were added to the residue and the reaction mixture was heated at 80° C. for 1.5 hours. Subsequently, the reaction solution was added with ethyl acetate and toluene, washed with saturated ammonium chloride aqueous solution and saturated brine, the organic layer was dried using sodium sulfate and the solvent was evaporated under reduced pressure. The residue was purified by silica gel chromatography (elution solvent: hexane/ethyl acetate=100/0 to 0/100 gradient) to obtain 4.61 g of cis-4- ethylcyclohexyl 4-(4-benzyloxy-3-methoxybenzylcarbamoyl)-piperidine-1-carboxylate.

(4) The product (4.61 g) of the above (3) was dissolved in ethanol (50 ml) and 10% palladium on carbon (160 mg) was added thereto to carry out catalytic hydrogenation at room temperature. After 12 hours, the catalyst was filtered, the solvent was evaporated and the residue was purified by silica gel chromatography (elution solvent: hexane/ethyl acetate=100/0 to 0/100 gradient) to obtain 2.83 g of an intended product.

(5) After dissolving the intended product obtained in the above (4) in ethyl acetate, heptane was added for crystallization, and the suspension was stirred and then filtered to obtain the crystal.

$^1$H-NMR (CDCl$_3$, δ): 0.88 (3H, t), 1.14-1.32 (5H, m), 1.44-1.79 (6H, m), 1.81-1.94 (4H, m), 2.21-2.34 (1H, m), 2.69-2.96 (2H, m), 3.88 (3H, s), 4.11-4.31 (2H, m), 4.36 (2H, d), 4.87-4.96 (1H, m), 5.60 (1H, s), 5.68 (1H, brs), 6.75 (1H, dd), 6.79 (1H, d), 6.86 (1H, d). m.p. 109° C. XRD: 2θ=6.5, 10.6, 13.0, 18.0, 20.0°

Examples 2-12

Using various substituted cyclohexanols instead of the cis-4-ethylcyclohexanol in Example 1, the compounds shown in Table 1 and Table 2 were obtained by reacting and treating in the same manner as in Example 1.

TABLE 1

| Example | Structural formula | $^1$H-NMR (CDCl$_3$, δ) (Melting point)(m.p.) (XRD) |
|---|---|---|
| Example 2 | MeO, HO-phenyl-CH$_2$-NH-C(O)-piperidine-N-C(O)-O-cyclohexyl-CH$_2$-Me | 0.87 (3H, t), 0.90-1.36 (7H, m), 1.60-1.88 (6H, m), 1.92-2.05 (2H, m), 2.18-2.30 (1H, m), 2.66-2.82 (2H, m), 3.88 (3H, s), 4.08-4.25 (2H, m), 4.35 (2H, d), 4.48-4.60 (1H, m), 5.59 (1H, s), 5.66 (1H, brs), 6.72 (1H, dd), 6.76 (1H, d), 6.86 (1H, d). ((m.p. 120° C.) (2 θ = 5.2, 7.5, 8.7, 14.9, 19.1°))* |
| Example 3 | MeO, HO-phenyl-CH$_2$-NH-C(O)-piperidine-N-C(O)-O-cyclohexyl-Me | 0.91 (3H, d), 1.11-1.29 (2H, m), 1.35-1.75 (7H, m), 1.77-1.91 (4H, m), 2.19-2.31 (1H, m), 2.68-2.87 (2H, m). 3.88 (3H, s), 4.10-4.29 (2H, m), 4.36 (2H, d), 4.86-4.93 (1H, m), 5.59 (1H, s), 5.87 (1H, brs), 6.76 (1H, dd), 6.79 (1H, d), 6.87 (1H, d). |
| Example 4 | MeO, HO-phenyl-CH$_2$-NH-C(O)-piperidine-N-C(O)-O-cyclohexyl-Me | 0.88 (3H, d), 0.94-1.10 (2H, m), 1.21-1.41 (3H, m), 1.60-1.76 (4H, m), 1.77-2.01 (4H, m), 2.18-2.30 (1H, m), 2.68-2.82 (2H, m), 3.88 (3H, s), 4.10-4.28 (2H, m), 4.35 (2H, d), 4.48-4.60 (1H, m), 5.59 (1H, s), 5.67 (1H, brs), 6.75 (1H, dd), 6.78 (1H, d), 6.87 (1H, d). |
| Example 5 | MeO, HO-phenyl-CH$_2$-NH-C(O)-piperidine-N-C(O)-O-cyclohexyl-C(Me)$_3$ | 0.85 (9H, s), 1.00-1.31 (4H, m), 1.39-1.71 (5H, m), 1.79-1.99 (4H, m), 2.20-2.31 (1H, m), 2.69-2.90 (2H, m), 3.88 (3H, s), 4.11-4.29 (2H, m), 4.36 (2H, d), 4.87-4.94 (1H, m), 5.62 (1H, s), 5.69 (1H, brs), 6.76 (1H, dd), 6.79 (1H, d), 6.87 (1H, d). |
| Example 6 | MeO, HO-phenyl-CH$_2$-NH-C(O)-piperidine-N-C(O)-O-cyclohexyl-C(Me)$_3$ | 0.76 (3H, s), 0.76 (3H, s), 1.11-1.38 (6H, m), 1.41-1.85 (10H, m), 2.20-2.31 (1H, m), 2.66-2.89 (2H, m), 3.88 (3H, s), 4.10-4.28 (2H, m), 4.35 (2H, d), 4.58-4.69 (1H, m), 5.64 (1H, s), 5.71 (1H, brs), 6.75 (1H, dd), 6.78 (1H, d), 6.86 (1H, d). |

*Crystallized solvent: ethyl acetate-heptane

TABLE 2

| Example | Structural formula | ¹H-NMR (CDCl₃, δ) (Melting Point)(m.p.) (XRD) |
|---|---|---|
| Example 7 | (3,4-MeO,OH-benzyl)NH-C(O)-piperidine-N-C(O)O-cyclohexyl-4,4-diethyl | 0.75 (3H, t), 0.76 (3H, t), 1.10-1.42 (6H, m), 1.43-1.91 (10H, m), 2.20-2.31 (1H, m), 2.69-2.90 (2H, m), 3.88 (3H, s), 4.11-4.29 (2H, m), 4.36 (2H, d), 4.87-4.94 (1H, m), 5.62 (1H, 5.69 (1H, brs), 6.76 (1H, dd), 8.79 (1H, d), 6.87 (1H, d). |
| Example 8 | (3,4-MeO,OH-benzyl)NH-C(O)-piperidine-N-C(O)O-cyclohexyl-4,4-dimethyl | 0.92 (6H, d), 1.18-1.48 (4H, m), 1.51-1.89 (8H, m), 2.19-2.30 (1H, m), 2.69-2.88 (2H, m), 3.88 (3H, s), 4.10-4.28 (2H, m), 4.36 (2H, d), 4.58-4.69 (1H, m), 5.60 (1H, s), 5.67 (1H, brs), 6.76 (1H, dd), 6.79 (1H, d), 6.87 (1H, d). ((m.p. 111° C.) (2 θ = 4.8, 8.4, 9.6, 20.0, 23.4°))* |
| Example 9 | (3,4-MeO,OH-benzyl)NH-C(O)-piperidine-N-C(O)O-cyclohexyl (R*,S*)-Me | 0.71-1.01 (2H, m), 0.91 (3H, d), 1.11-1.38 (4H, m), 1.39-2.03 (7H, m), 2.19-2.31 (1H, m), 2.69-2.85 (2H, m), 3.88 (3H, s), 4.10-4.29 (2H, m), 4.35 (2H, d), 4.61-4.69 (1H, m), 5.60 (1H, s), 5.66 (1H, brs), 6.75 (1H, dd), 6.79 (1H, d), 6.87 (1H, d). |
| Example 10 | (3,4-MeO,OH-benzyl)NH-C(O)-piperidine-N-C(O)O-cyclohexyl (S*,S*)-Me | 0.88 (3H, d), 0.89-1.24 (2H, m), 1.35-1.90 (11H, m), 2.20-2.32 (1H, m), 2.69-2.87 (2H, m), 3.88 (3H, s), 4.12-4.31 (2H, m), 4.36 (2H, d), 4.95-5.02 (1H, m), 5.59 (1H, s), 5.65 (1H, brs), 6.75 (1H, dd), 6.79 (1H, d), 6.87 (1H, d). |
| Example 11 | (3,4-MeO,OH-benzyl)NH-C(O)-piperidine-N-C(O)O-cyclohexyl-2-Me (R*,S*) | 0.88 (3H, d), 1.23-1.50 (6H, m), 1.53-1.91 (7H, m), 2.20-2.33 (1H, m), 2.70-2.91 (2H, m), 3.88 (3H, s), 4.15-4.29 (2H, m), 4.36 (2H, d), 4.79-4.85 (1H, m), 5.60 (1H, s), 5.68 (1H, brs), 6.75 (1H, dd), 6.79 (1H, d), 6.87 (1H, d). |
| Example 12 | (3,4-MeO,OH-benzyl)NH-C(O)-piperidine-N-C(O)O-cyclohexyl-3,5-diMe | 0.51-1.69 (1H, m), 0.88 (6H, d), 0.94-1.06 (2H, m), 1.55-1.90 (9H, m), 2.19-2.32 (1H, m), 2.69-2.89 (2H, m), 3.88 (3H, s), 4.10-4.30 (2H, m), 4.36 (2H, d), 4.97-5.04 (1H, m), 5.58 (1H, s), 5.65 (1H, brs), 6.75 (1H, dd), 6.79 (1H, d), 6.87 (1H, d). |

*Crystallized solvent: ethanol-water

Example 13

Preparation of cis-2-ethylcyclohexyl 4-(4-hydroxy-3-methoxybenzylcarbamoyl)-piperidine-1-carboxylate

[Chemical Formula 10]

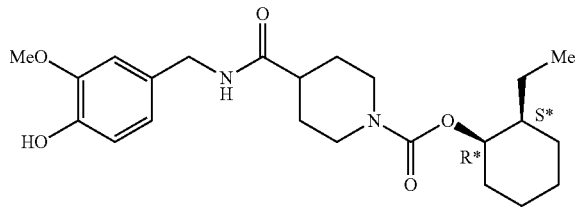

Using 2-ethylcyclohexanol instead of the cis-4-ethylcyclohexanol in Example 1, the reaction and treatment were carried out in the same manner as in Example 1. Then, the cis isomer was separated and formed by silica gel column chromatography (elution solvent: hexane/ethyl acetate=100/0 to 0/100 gradient) to obtain an intended product.

$^1$H-NMR (CDCl$_3$, δ): 0.88 (3H, t), 1.15-1.84 (11H, m), 1.85-1.98 (4H, m), 2.21-2.34 (1H, m), 2.68-2.94 (2H, m), 3.88 (3H, s), 4.11-4.30 (2H, m), 4.36 (2H, d), 4.89-4.97 (1H, m), 5.59 (1H, s), 5.66 (1H, brs), 6.75 (1H, dd), 6.78 (1H, d), 6.87 (1H, d).

Example 14

Preparation of 4,4-diethylcyclohexyl 3-(4-hydroxy-3-methoxybenzylcarbamoyl)-azetidine-1-carboxylate

[Chemical Formula 11]

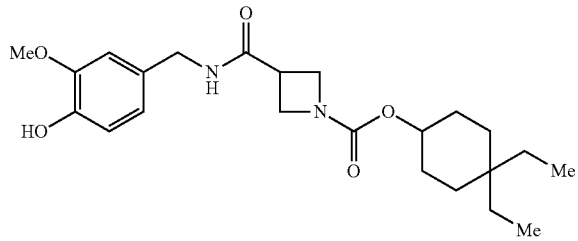

(1) A mixture of t-butyldicarbonate (21.15 g) and THF (170 ml) was added under ice cooling to a mixture of azetidine-3-carboxylic acid (9.80 g), potassium carbonate (26.8 g) and water (150 ml). After stirring the reaction mixture at room temperature for 20 hours, the mixture was adjusted to pH 4 using 2 mol/L hydrochloric acid, extracted with chloroform, the organic layer was dried over sodium sulfate and the solvent was evaporated under reduced pressure. The residue was crystallized with a mixed solution of hexane and ethyl acetate to obtain 19.5 g of 1-(t-butoxycarbonyl)azetidine-3-carboxylic acid.

(2) 1-Ethyl-3-(3-dimethylaminopropyl)carbodiimide hydrochloride (7.84 g) was added to a mixture of the product (6.33 g) of the above (1), 4-benzyloxy-3-methoxy benzylamine hydrochloride (8.80 g), triethylamine (5.70 ml) and methylene chloride (160 ml). After stirring the reaction mixture at room temperature for 20 hours, the mixture was washed with saturated ammonium chloride aqueous solution and then saturated brine, the organic layer was dried over sodium sulfate and the solvent was evaporated under reduced pressure. The residue was purified by silica gel chromatography (elution solvent: hexane/ethyl acetate=100/0 to 0/100 gradient) to obtain 9.71 g of t-butyl 3-(4-benzyloxy-3-methoxybenzylcarbamoyl)-azetidine-1-carboxylate.

(3) The product (9.71 g) of the above (2) was dissolved in methylene chloride (70 ml) and trifluoroacetic acid (20 ml) was added thereto under ice cooling. The reaction mixture was stirred at room temperature for 1.5 hours, neutralized with a sodium hydrate aqueous solution, extracted with chloroform and washed with saturated brine. The organic layer was dried over sodium sulfate, the solvent was evaporated under reduced pressure, and the residue was crystallized with a mixed solution of hexane and ethyl acetate to obtain 7.46 g of N-(4-benzyloxy-3-methoxybenzyl)-3-azetidinecarboxamide.

(4) N,N'-carbonyldiimidazole (2.69 g) was added to a mixture of 4,4-diethylcyclohexanol (2.00 g) and methylene chloride (70 ml). After stirring the reaction mixture at room temperature for 20 hours, the mixture was washed with water twice, the organic layer was dried over sodium sulfate and the solvent was evaporated under reduced pressure. The product (3.56 g) of the above (3), triethylamine (3.04 ml), 4-dimethylaminopyridine (100 mg) and DMF (50 ml) were added to the residue and the reaction mixture was heated at 60° C. for 3 hours. The reaction mixture was added with ethyl acetate and toluene, washed with saturated ammonium chloride aqueous solution and then saturated brine, the organic layer was dried over sodium sulfate and the solvent was evaporated under reduced pressure. The residue was purified by silica gel chromatography (elution solvent: hexane/ethyl acetate=100/0 to 0/100 gradient) to obtain 3.25 g of 4,4-diethylcyclohexyl 3-(4-benzyloxy-3-methoxybenzylcarbamoyl)-azetidine-1-carboxylate.

(5) The product (3.25 g) of the above (4) was dissolved in ethanol (70 ml) and 10% palladium on carbon (120 mg) was added thereto to carry out catalytic hydrogenation at room temperature. After 3 hours, the catalyst was filtered, the solvent was evaporated and the residue was purified by silica gel chromatography (elution solvent: hexane/ethyl acetate=100/0 to 0/100 gradient) to obtain 2.83 g of an intended product.

(6) After dissolving the intended product obtained in the above (5) in ethyl acetate, heptane was added for crystallization, and the suspension was stirred and filtered to obtain the crystal.

$^1$H-NMR (CDCl$_3$, δ): 0.74 (3H, t), 0.75 (3H, t), 1.10-1.40 (6H, m), 1.41-1.59 (4H, m), 1.61-1.80 (2H, m), 3.12-3.27 (1H, m), 3.89 (3H, s), 4.03-4.22 (4H, m), 4.38 (2H, d), 4.55-4.66 (1H, m), 5.60 (1H, s), 5.67 (1H, brs), 6.76 (1H, dd), 6.80 (1H, d), 6.87 (1H, d). m.p. 95° C. XRD: 2θ=5.6, 11.2, 13.4, 14.5, 16.8°.

Examples 15-21

Using various substituted cyclohexanols instead of the 4,4-ethylcyclohexanol in Example 14, the compounds shown in Table 3 were obtained by reacting and treating in the same manner as in Example 14.

TABLE 3

| Example | Structural formula | $^1$H-NMR (CDCl$_3$, δ) (Melting point)(m.p.) (XRD) |
|---|---|---|
| Example 15 | (structural formula) | 0.88 (3H, s), 1.12-1.35 (5H, m), 1.42-1.61 (4H, m), 1.76-1.90 (2H, m), 3.14-3.27 (1H, m), 3.89 (3H, s), 4.08-4.27 (4H, m), 4.38 (2H, d), 4.83-4.90 (1H, m), 5.61 (1H, s), 5.68 (1H, brs), 6.76 (1H, dd), 6.79 (1H, d). 6.87 (1H, d). |
| Example 16 | (structural formula) | 0.85 (9H, s), 0.94-1.05 (1H, m), 1.16-1.62 (6H, m), 1.87-2.00 (2H, m), 3.14-3.28 (1H, m), 3.89 (3H, s), 4.09-4.28 (4H, m), 4.38 (2H, d), 4.86-4.93 (1H, m), 5.61 (1H, s), 5.69 (1H, brs), 6.76 (1H, dd), 6.79 (1H, d), 6.87 (1H, d), ((Crystal A m.p. 112° C. (2 θ = 4.7, 9.4, 14.1, 16.9, 20.2°)) (Crystal B m.p. 113° C. 2 θ = 4.7, 9.3, 11.6, 16.8, 18.4°)))* |
| Example 17 | (structural formula) | 0.84 (9H, s), 0.91-1.32 (5H, m), 1.71-1.82 (2H, m), 1.97-2.06 (2H, m), 3.13-3.28 (1H, m), 3.89 (3H, s), 4.04-4.21 (4H, m), 4.38 (2H, d), 4.41-4.54 (1H, m), 5.81 (1H, s), 5.68 (1H, brs), 6.76 (1H, dd), 8.79 (1H, d), 6.87 (1H, d). |
| Example 18 | (structural formula) | 0.87 (3H, s), 0.88-1.40 (4H, m), 1.41-1.82 (7H, m), 3.13-3.28 (1H, m), 3.80 (3H, s), 4.02-4.25 (4H, m), 4.37 (2H, d), 4.83-4.90 (1H, m), 5.78 (1H, s), 5.90 (1H, brs), 6.76 (1H, dd), 6.79 (1H, d), 6.87 (1H, d). |
| Example 19 | (structural formula) | 0.93 (6H, s), 1.04 (6H, s), 1.04-1.27 (4H, m), 1.69-1.79 (2H, m), 3.13-3.27 (1H, m), 3.89 (3H, s), 4.05-4.24 (4H, m), 4.38 (2H, d), 4.84-4.94 (1H, m), 5.61 (1H, s), 5.67 (1H, brs), 6.76 (1H, dd), 6.79 (1H, d), 6.87 (1H, d). |
| Example 20 | (structural formula) | 0.78 (3H, s), 0.88 (3H, s), 0.90 (3H, s), 0.90-1.12 (3H, m), 1.21-1.69 (4H, m), 1.70-2.07 (2H, m), 3.12-3.27 (1H, m), 3.89 (3H, s), 4.04-4.22 (4H, m), 4.38 (2H, d), 4.52 (1H, dt), 5.61 (1H, s), 5.68 (1H, brs), 6.76 (1H, dd), 6.80 (1H, d), 6.87 (1H, d). |

TABLE 3-continued

| Example | Structural formula | ¹H-NMR (CDCl₃, δ) (Melting point)(m.p.) (XRD) |
|---|---|---|
| Example 21 | 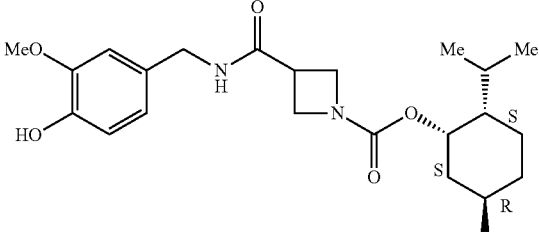 | 0.86 (3H, s), 0.88 (3H, s), 0.90 (3H, s), 0.90-1.07 (2H, m), 1.19-1.75 (5H, m), 1.88-2.00 (2H, m), 3.18-3.28 (1H, m), 3.89 (3H, s), 4.03-4.23 (4H, m), 4.39 (2H, d), 4.99-5.07 (1H, m), 5.62 (1H, s), 5.67 (1H, brs), 6.76 (1H, dd), 6.80 (1H, d), 6.88 (1H, d). |

*Crystal A crystallized solvent: ethyl acetate-heptane
Crystal B crystallized solvent: acetone-water

Examples 22-25

Using 4-butylcyclohexanol or 4-(isopropyl)cyclohexanol instead of 4,4-diethylcyclohexanol in Example 14, the reaction and treatment were carried out in the same manner as in Example 14. Subsequently, the cis isomer and trans isomer were separated and purified by silica gel column chromatography (elution solvent: hexane/ethyl acetate=100/0 to 0/100 gradient) to obtain the compounds shown in Table 4.

TABLE 4

| Example | Structural formula | ¹H-NMR (CDCl₃, δ) |
|---|---|---|
| Example 22 | 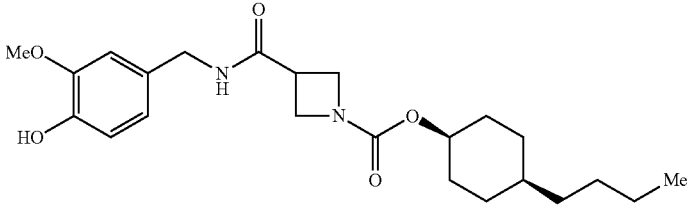 [SMILES: CCCC[C@H]1CC[C@@H](OC(=O)N2CC(C(=O)NCc3ccc(O)c(OC)c3)C2)CC1] | 0.89 (3H, s), 1.15-1.38 (9H, m), 1.41-1.68 (4H, m), 1.78-1.91 (2H, m), 3.15-3.27 (1H, m), 3.89 (3H, s), 4.06-4.26 (4H, m), 4.38 (2H, d), 4.84-4.91 (1H, m), 5.80 (1H, s), 5.67 (1H, brs), 6.76 (1H, dd), 6.79 (1H, d), 6.88 (1H, d). |
| Example 23 | 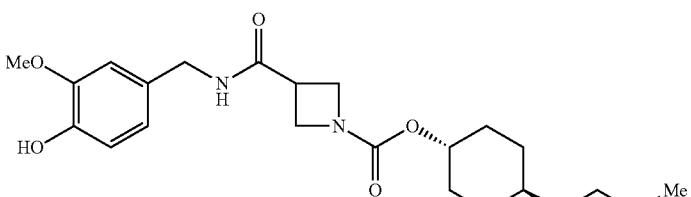 | 0.88 (3H, s), 0.90-1.35 (11H, m), 1.70-1.81 (2H, m), 1.89-2.00 (2H, m), 3.14-3.26 (1H, m), 3.89 (3H, s), 4.04-4.22 (4H, m), 4.38 (2H, d), 4.45-4.58 (1H, m), 5.67 (1H, s), 5.68 (1H, brs), 6.76 (1H, dd), 6.80 (1H, d), 6.87 (1H, d). |
| Example 24 | 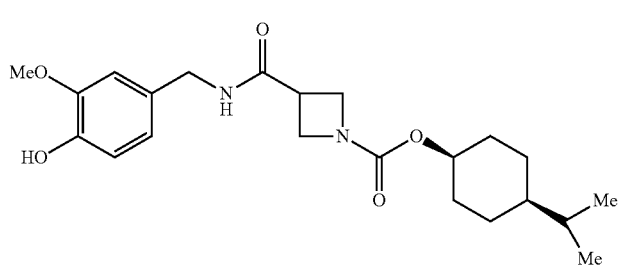 [SMILES: COc1cc(CNC(=O)C2CN(C(=O)O[C@H]3CC[C@@H](C(C)C)CC3)C2)ccc1O] | 0.87 (6H, s), 0.97-1.12 (1H, m), 1.19-1.59 (7H, m), 1.80-1.91 (2H, m), 3.15-3.27 (1H, m), 3.89 (3H, s), 4.06-4.25 (4H, m), 4.39 (2H, d), 4.85-4.91 (1H, m), 5.60 (1H, s), 5.67 (1H, brs), 6.77 (1H, dd), 6.80 (1H, d), 6.88 (1H, d). |
| Example 25 | 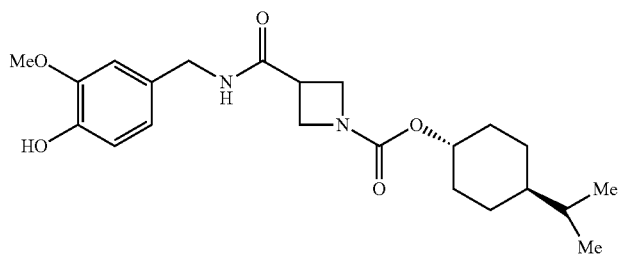 [SMILES: COc1cc(CNC(=O)C2CN(C(=O)O[C@H]3CC[C@H](C(C)C)CC3)C2)ccc1O] | 0.85 (6H, s), 0.98-1.17 (3H, m), 1.20-1.51 (3H, m), 1.68-1.77 (2H, m), 1.94-2.05 (2H, m), 3.12-3.25 (1H, m), 3.89 (3H, s), 4.04-4.20 (4H, m), 4.38 (2H, d), 4.44-4.57 (1H, m), 5.60 (1H, s), 5.67 (1H, brs), 6.76 (1H, dd), 6.80 (1H, d), 6.87 (1H, d). |

Example 26

Preparation of (1R,2S,5R)-2-isopropenyl-5-methyl-cyclohexyl 3-(4-hydroxy-3-methoxybenzylcarbamoyl)-azetidine-1-carboxylate

[Chemical Formula 12]

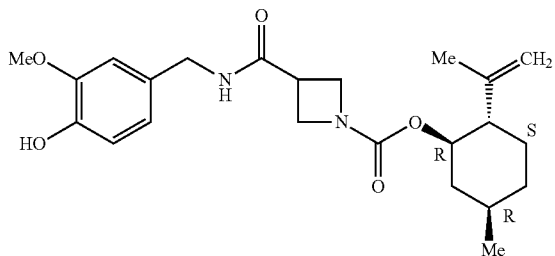

(1) The N-(4-benzyloxy-3-methoxybenzyl)-3-azetidinecarboxamide (386 mg) of Example 14 (3) was dissolved in a mixture of ethanol (10 ml), acetic acid (0.5 ml) and methanol (5 ml), and 10% palladium on carbon (30 mg) was added thereto to carry out catalytic hydrogenation at room temperature. After 1 hour, the catalyst was filtered and the solvent was evaporated to obtain 270 mg of N-(4-hydroxy-3-methoxybenzyl)-3-azetidinecarboxamide.

(2) N,N'-carbonyldiimidazole (248 mg) was added to a mixture of (1R,2S,5R)-2-isopropenyl-5-methylcyclohexanol (182 mg) and acetonitrile (10 ml). The reaction mixture was stirred at 60° C. for 1 hour, added with water and chloroform and washed with water. The organic layer was dried over sodium sulfate and the solvent was evaporated under reduced pressure. The product (270 mg) of the above (1), triethylamine (0.56 ml), 4-dimethylaminopyridine (15 mg) and DMF (8 ml) were added to the residue and the reaction solution was heated at 80° C. for 1 hour. The reaction mixture was evaporated under reduced pressure, and water and chloroform were added thereto. The organic layer was dried over sodium sulfate and the solvent was evaporated under reduced pressure. The residue was purified by silica gel chromatography (elution solvent: hexane/ethyl acetate=100/0 to 0/100 gradient) to obtain 65 mg of an intended product.

$^1$H-NMR (CDCl$_3$, δ): 0.81-1.12 (2H, m), 0.92 (3H, s), 1.30-1.71 (4H, m), 1.67 (3H, s), 1.89-2.10 (2H, m), 3.11-3.26 (1H, m), 3.89 (3H, s), 4.00-4.21 (4H, m), 4.38 (2H, d), 4.61 (1H, dt), 4.69-4.80 (2H, m), 5.60 (1H, s), 5.66 (1H, brs), 6.76 (1H, dd), 6.80 (1H, d), 6.87 (1H, d).

Example 27

Preparation of 4,4-dimethylcyclohexyl (S)-3-(4-hydroxy-3-methoxybenzylcarbamoyl)-pyrrolidine-1-carboxylate

[Chemical Formula 13]

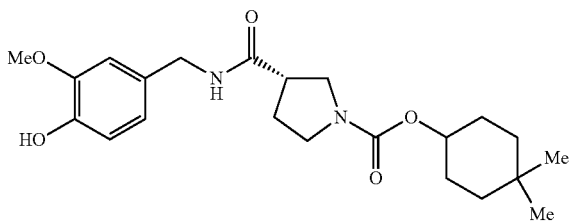

(1) 1-Ethyl-3-(3-dimethylaminopropyl)carbodiimide hydrochloride (1.12 g) was added to a mixture of 4-benzyloxy-3-methoxybenzylamine hydrochloride (1.26 g), (S)-1-(t-butoxycarbonyl)pyrrolidine-3-carboxylic acid (0.97 g), triethylamine (0.82 ml) and methylene chloride (20 ml). After stirring the reaction mixture at room temperature for 20 hours, the mixture was washed with saturated ammonium chloride aqueous solution and then saturated brine, the organic layer was dried over sodium sulfate and the solvent was evaporated under reduced pressure. The residue was purified by silica gel chromatography (elution solvent: hexane/ethyl acetate=100/0 to 0/100 gradient) to obtain 1.42 g of t-butyl (S)-3-(4-benzyloxy-3-methoxybenzylcarbamoyl)-piperidine-1-carboxylate.

(2) The product (1.42 g) of the above (1) was dissolved in ethyl acetate (27 ml) and 4 mol/l hydrogen chloride/ethyl acetate (9 ml) was added thereto. After stirring the reaction mixture for 6 hours, hexane (36 ml) was added to the mixture and the precipitated crystal was filtered to obtain 1.16 g of (S)-N-(4-benzyloxy-3-methoxybenzyl)-3-piperidinecarboxamide.

(3) N,N'-carbonyldiimidazole (118 mg) was added to a mixture of 4,4-dimethylcyclohexanol (72 mg) and acetonitrile (7 ml). The reaction mixture was stirred at 45° C. for 1 hour, added with water and chloroform and washed with water. The organic layer was dried over sodium sulfate and the solvent was evaporated under reduced pressure. The product (190 mg) of the above (2), triethylamine (0.21 ml), 4-dimethylaminopyridine (10 mg) and DMF (5 ml) were added to the residue and the reaction mixture was heated at 80° C. for 1 hour. The reaction mixture was evaporated under reduced pressure, and water and chloroform were added thereto. The organic layer was dried over sodium sulfate and the solvent was evaporated under reduced pressure. The residue was purified by silica gel chromatography (elution solvent: hexane/ethyl acetate=100/0 to 0/100 gradient) to obtain 135 mg of 4,4-dimethylcyclohexyl (S)-3-(4-benzyloxy-3-methoxybenzylcarbamoyl)-piperidine-1-carboxylate.

(4) The product (135 mg) of the above (3) was dissolved in ethanol (7 ml) and 10% palladium on carbon (10 mg) was added thereto to carry out catalytic hydrogenation at room temperature. After 1 hour, the catalyst was filtered, the solvent was evaporated and the residue was purified by silica gel chromatography (elution solvent: hexane/ethyl acetate=100/0 to 0/100 gradient) to obtain 72 mg of an intended product.

$^1$H-NMR (CDCl$_3$, δ): 0.92 (6H, s), 1.19-1.34 (3H, m), 1.37-1.62 (3H, m), 1.68-1.79 (2H, m), 2.06-2.28 (2H, m), 2.77-2.94 (1H, m), 3.32-3.45 (1H, m), 3.52-3.76 (3H, m), 3.89 (3H, s), 4.37 (2H, d), 4.58-4.69 (1H, m), 5.61 (1H, s), 5.72 (1H, brs), 6.77 (1H, dd), 6.79 (1H, d), 6.88 (1H, d).

Examples 28-30

Using various substituted cyclohexanols instead of the 4,4-dimethylcyclohexanol in Example 27, the compounds shown in Table 5 were obtained by reacting and treating in the same manner as in Example 27.

TABLE 5

| Example | Structural formula | $^1$H-NMR (CDCl$_3$, δ) |
|---|---|---|
| Example 28 | (structure: MeO, HO-phenyl-CH$_2$-NH-C(O)-pyrrolidine-N-C(O)O-cyclohexyl-Et, Me) | 0.88 (3H, s), 1.14-1.29 (5H, m), 1.39-1.59 (4H, m), 1.78-1.89 (2H, m), 2.05-2.27 (2H, m), 2.78-2.93 (1H, m), 3.31-3.45 (1H, m), 3.49-3.76 (3H, m), 3.89 (3H, s), 4.37 (2H, d), 4.87-4.96 (1H, m), 5.60 (1H, s), 5.73 (1H, brs), 6.77 (1H, dd), 6.79 (1H, d), 6.88 (1H, d). |
| Example 29 | (structure with 4,4-diethyl cyclohexyl) | 0.75 (3H, t), 0.76 (3H, t), 1.10-1.34 (6H, m), 1.36-1.60 (4H, m), 1.83-1.77 (2H, m), 2.00-2.24 (2H, m), 2.75-2.91 (1H, m), 3.30-3.45 (1H, m), 3.47-3.72 (3H, m), 3.89 (3H, s), 4.37 (2H, d). 4.58-4.71 (1H, m), 5.60 (1H, s), 5.72 (1H, brs), 6.76 (1H, dd), 6.79 (1H, d), 6.88 (1H, d). |
| Example 30 | (structure with 4-t-butyl cyclohexyl) | 0.83 (9H, s), 0.98-1.38 (4H, m), 1.40-1.61 (3H, m), 1.88-1.98 (2H, m), 2.02-2.19 (2H, m), 2.78-2.92 (1H, m), 3.31-3.44 (1H, m), 3.50-3.73 (3H, m), 3.89 (3H, s), 4.37 (2H, d), 4.89-4.95 (1H, m), 5.60 (1H, s), 5.72 (1H, brs), 6.77 (1H, dd), 6.79 (1H, d), 6.88 (1H, d). |

Example 31

Preparation of 4,4-dimethylcyclohexyl (R)-3-(4-hydroxy-3-methoxybenzylcarbamoyl)-pyrrolidine-1-carboxylate

[Chemical Formula 14]

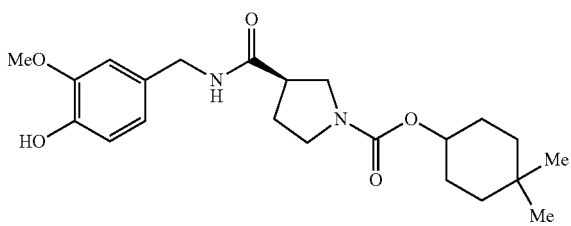

Using (R)-1-(t-butoxycarbonyl)pyrrolidine-3-carboxylic acid instead of the (S)-1-(t-butoxycarbonyl)pyrrolidine-3-carboxylic acid in Example 27, the reaction and treatment were carried out in the same manner as in Example 27.

$^1$H-NMR (CDCl$_3$, δ): 0.92 (6H, s), 1.19-1.32 (3H, m), 1.37-1.62 (3H, m), 1.68-1.79 (2H, m), 2.05-2.27 (2H, m), 2.77-2.94 (1H, m), 3.32-3.45 (1H, m), 3.52-3.76 (3H, m), 3.89 (3H, s), 4.37 (2H, d), 4.58-4.69 (1H, m), 5.60 (1H, s), 5.72 (1H, brs), 6.77 (1H, dd), 6.79 (1H, d), 6.88 (1H, d).

Examples 32-34

Using various substituted cyclohexanols instead of the 4,4-dimethylcyclohexanol in Example 31, the compounds shown in Table 6 were obtained by reacting and treating in the same manner as in Example 31.

TABLE 6

| Example | Structural formula | $^1$H-NMR (CDCl$_3$, δ) |
|---|---|---|
| Example 32 | (structure with 4-ethyl cyclohexyl) | 0.88 (3H, s), 1.14-1.29 (5H, m), 1.39-1.59 (4H, m), 1.78-1.89 (2H, m), 2.04-2.27 (2H, m), 2.76-2.92 (1H, m), 3.31-3.45 (1H, m), 3.49-3.76 (3H, m), 3.89 (3H, s), 4.37 (2H, d), 4.87-4.96 (1H, m), 5.59 (1H, s), 5.73 (1H, brs), 6.77 (1H, dd), 6.79 (1H, d), 6.88 (1H, d). |

TABLE 6-continued

| Example | Structural formula | $^1$H-NMR (CDCl$_3$, δ) |
|---------|-------------------|--------------------------|
| Example 33 | | 0.75 (3H, t), 0.76 (3H, t), 1.10-1.34 (6H, m), 1.36-1.60 (4H, m), 1.62-1.76 (2H, m), 2.01-2.25 (2H, m), 2.75-2.91 (1H, m), 3.30-3.45 (1H, m), 3.47-3.72 (3H, m), 3.89 (3H, s), 4.37 (2H, d), 4.59-4.72 (1H, m), 5.60 (1H, s), 5.72 (1H, brs), 6.76 (1H, dd), 6.79 (1H, d), 6.88 (1H, d). |
| Example 34 | | 0.85 (9H, s), 0.97-1.38 (4H, m), 1.38-1.61 (3H, m), 1.88-1.98 (2H, m), 2.02-2.19 (2H, m), 2.76-2.92 (1H, m), 3.31-3.44 (1H, m), 3.50-3.73 (3H, m), 3.89 (3H, s), 4.37 (2H, d), 4.89-4.95 (1H, m), 5.59 (1H, s), 5.73 (1H, brs), 6.77 (1H, dd), 6.79 (1H, d), 6.88 (1H, d). |

Example 35

Preparation of (1R,3R)-3-methylcyclohexyl 4-(4-hydroxy-3-methoxybenzylcarbamoyl)-piperidine-1-carboxylate

[Chemical Formula 15]

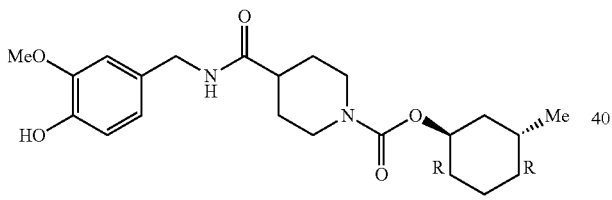

(1) 3N Hydrochloric acid (25 ml) was added to (+)-pulegone (5.00 g), the reaction mixture was refluxed with heating for 5 hours and water and diethyl ether were added to the reaction mixture. The organic layer was washed with saturated brine, dried over sodium sulfate and the solvent was evaporated under reduced pressure to obtain (R)-3-methylcyclohexanone.

(2) Under nitrogen atmosphere, the product (3.69 g) of the above (1) was dissolved in anhydrous THF (90 ml), the obtained reaction mixture was cooled to −78° C. and a THF solution containing 1M lithium tri-sec-butylborohydride was added thereto over a period of 20 minutes. After raising the temperature of the reaction mixture to about −30° C. over a period of 2 hours, a saturated ammonium chloride aqueous solution was added thereto, followed by the extraction using diethyl ether. After drying the organic layer with sodium sulfate, the solvent was evaporated under reduced pressure and the residue was purified by silica gel chromatography (elution solvent: hexane/ethyl acetate=100/0 to 0/100 gradient) to obtain 2.95 g of (1R,3R)-3-methylcyclohexanol.

(3) Subsequently, using the product of the above (2) instead of the cis-4-ethylcyclohexanol in Example 1, the reaction and treatment were carried out in the same manner as in Example 1 to obtain an intended product.

(4) After dissolving the intended product of the above (3) in ethyl acetate, heptane was added to crystallize the product and the suspension was stirred and filtered to obtain the crystal.

$^1$H-NMR (CDCl$_3$, δ): 0.88 (3H, d), 0.89-1.24 (2H, m), 1.35-1.90 (11H, m), 2.21-2.33 (1H, m), 2.69-2.87 (2H, m), 3.88 (3H, s), 4.11-4.31 (2H, m), 4.36 (2H, d), 4.95-5.02 (1H, m), 5.59 (1H, s), 5.65 (1H, brs), 6.75 (1H, dd), 6.79 (1H, d), 6.87 (1H, d). m.p. 155° C. XRD: 2θ=6.9, 12.8, 14.8, 18.0, 20.7°.

Example 36

Preparation of (1S,3S)-3-methylcyclohexyl 4-(4-hydroxy-3-methoxybenzylcarbamoyl)-piperidine-1-carboxylate

[Chemical Formula 16]

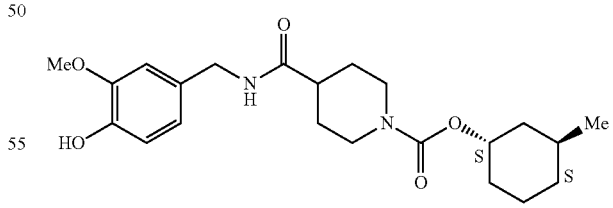

Using (−)-pulegone in place of (+)-pulegone in Example 35, the reaction and treatment were carried out in the same manner as in Example 35 to obtain an intended product.

$^1$H-NMR (CDCl$_3$, δ): 0.88 (3H, d), 0.89-1.24 (2H, m), 1.35-1.90 (11H, m), 2.20-2.32 (1H, m), 2.69-2.87 (2H, m), 3.88 (3H, s), 4.12-4.31 (2H, m), 4.36 (2H, d), 4.94-5.01 (1H, m), 5.59 (1H, s), 5.65 (1H, brs), 6.75 (1H, dd), 6.79 (1H, d), 6.87 (1H, d).

Example 37

Preparation of (1R,2S)-2-methylcyclohexyl 4-(4-hydroxy-3-methoxybenzylcarbamoyl)-piperidine-1-carboxylate

[Chemical Formula 17]

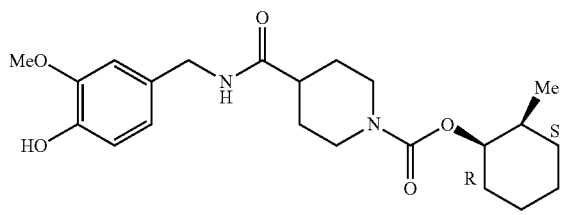

(1) A mixture of 2-methylcyclohexanone (13.1 g), (2R,4R)-2,4-pentanediol (12.2 g), pyridinium p-toluene sulfonate (119 mg) and toluene (120 ml) was refluxed with heating for 8 hours. The reaction mixture was added with a saturated aqueous solution of sodium hydrogen carbonate, extracted with diethyl ether, the organic layer was dried over sodium sulfate and the solvent was evaporated under reduced pressure. The residue was purified by silica gel chromatography (elution solvent: hexane/ethyl acetate=100/0 to 0/100 gradient) to obtain 18.0 g of (2R,4R)-2,4,7-trimethyl-1,5-dioxaspiro[5.5]undecane (2) Under nitrogen atmosphere, the product (18.0 g) of the above (1) was dissolved in anhydrous methylene chloride (550 ml), the obtained reaction mixture was cooled to 0° C. and added over a period of 20 minutes to a toluene solution containing 1M diisobutyl aluminum hydride. After stirring the reaction mixture for 1 hour, a saturated ammonium chloride aqueous solution was added thereto, the mixture was subjected to celite filtration and the filtrate was extracted with chloroform. After drying the organic layer with sodium sulfate, the solvent was evaporated under reduced pressure. The residue was purified by silica gel chromatography (elution solvent: hexane/ethyl acetate=100/0 to 0/100 gradient) to obtain 6.50 g of (2R,4R,7S)-2,4,7-trimethyl-1,5-dioxaspiro[5.5]undecane.

(3) The product (6.50 g) of the above (2) was dissolved in acetone (80 ml), the reaction mixture was cooled to 0° C. and 0.2N hydrochloric acid (10.8 ml) was added thereto, followed by stirring for 2 hours. Water and diethyl ether were added to the reaction mixture, the organic layer was dried over sodium sulfate and the solvent was evaporated under reduced pressure to obtain 3.68 g of (S)-2-methylcyclohexanone.

(4) Under nitrogen atmosphere, the product (3.68 g) of the above (3) was dissolved in anhydrous THF (130 ml), the obtained reaction mixture was cooled to −78° C. and a THF solution containing 1M lithium tri-sec-butylborohydride was added thereto over a period of 15 minutes. After raising the temperature of the reaction mixture to about 0° C. over a period of 3 hours, a saturated ammonium chloride aqueous solution was added thereto, followed by the extraction using diethyl ether. After drying the organic layer with sodium sulfate, the solvent was evaporated under reduced pressure and the residue was purified by silica gel chromatography (elution solvent: hexane/ethyl acetate=100/0 to 0/100 gradient) to obtain 2.98 g of (1R,2S)-2-methylcyclohexanol.

(5) Subsequently, using the product of the above (4) in place of the cis-4-ethylcyclohexanol in Example 1, the reaction and treatment were carried out in the same manner as in Example 1 to obtain an intended product.

(6) After dissolving the intended product of the above (5) in ethyl acetate, heptane was added to crystallize the product and the suspension was stirred and filtered to obtain crystal A. Tert-butylmethyl ether was added to the crystal A to give a suspension, which was stirred and then filtered to obtain crystal B. Further, ethanol-water was added to the crystal A to give a suspension, which was stirred and then filtered to obtain crystal C.

$^1$H-NMR (CDCl$_3$, δ): 0.88 (3H, d), 1.23-1.50 (6H, m), 1.53-1.91 (7H, m), 2.19-2.32 (1H, m), 2.69-2.91 (2H, m), 3.88 (3H, s), 4.14-4.29 (2H, m), 4.36 (2H, d), 4.79-4.85 (1H, m), 5.60 (1H, s), 5.68 (1H, brs), 6.75 (1H, dd), 6.79 (1H, d), 6.87 (1H, d). Crystal A m.p. 125° C., XRD: 2θ=6.0, 10.5, 12.0, 15.6, 21.1°. Crystal B m.p. 118° C., XRD: 2θ=6.2, 7.1, 9.0, 10.6, 16.8°. Crystal C m.p. 124° C. XRD: 2θ=6.1, 6.6, 7.5, 8.6, 15.7°.

Example 38

Preparation of (1S,2R)-2-methylcyclohexyl 4-(4-hydroxy-3-methoxybenzylcarbamoyl)-piperidine-1-carboxylate

[Chemical Formula 18]

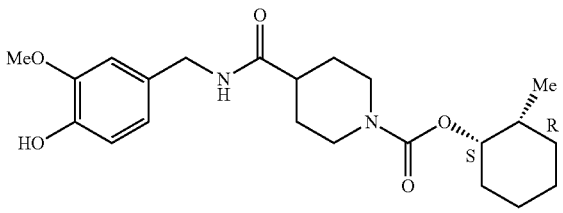

(3) Using (2S,4S)-2,4-pentanediol instead of the (2R,4R)-2,4-pentadiol in Example 37, the reaction and treatment were carried out in the same manner as in Example 37 to obtain an intended product.

$^1$H-NMR (CDCl$_3$, δ): 0.88 (3H, d), 1.23-1.50 (6H, m), 1.53-1.91 (7H, m), 2.20-2.33 (1H, m), 2.70-2.91 (2H, m), 3.88 (3H, s), 4.15-4.30 (2H, m), 4.36 (2H, d), 4.78-4.85 (1H, m), 5.61 (1H, s), 5.68 (1H, brs), 6.75 (1H, dd), 6.79 (1H, d), 6.87 (1H, d).

Examples 39 and 40

Using cycloheptanol or cyclohexylmethanol instead of the cis-4-ethylcyclohexanol in Example 1, the compounds shown in Table 7 were obtained by reacting and treating in the same manner as in Example 1.

TABLE 7

| Example | Structural formula | $^1$H-NMR (CDCl$_3$, δ) |
|---|---|---|
| Example 39 | | 1.35-1.74 (12H, m), 1.75-1.96 (4H, m), 2.18-2.30 (1H, m), 2.68-2.89 (2H, m), 3.88 (3H, s), 4.10-4.29 (2H, m), 4.36 (2H, d), 4.78-4.90 (1H, m), 5.58 (1H, s), 5.65 (1H, brs), 6.75 (1H, dd), 6.79 (1H, d), 6.87 (1H, d). |
| Example 40 | | 0.88-1.02 (2H, m), 1.10-1.29 (5H, m), 1.58-1.90 (8H, m), 2.18-2.31 (1H, m), 2.69-2.88 (2H, m), 3.87 (2H, d), 3.88 (3H, s), 4.08-4.26 (2H, m), 4.36 (2H, d), 5.59 (1H, s), 5.66 (1H, brs), 6.75 (1H, dd), 6.79 (1H, d), 6.87 (1H, d). |

Example 41

Preparation of 2-isopropylphenyl 4-(4-hydroxy-3-methoxybenzylcarbamoyl)-piperidine-1-carboxylate

[Chemical Formula 19]

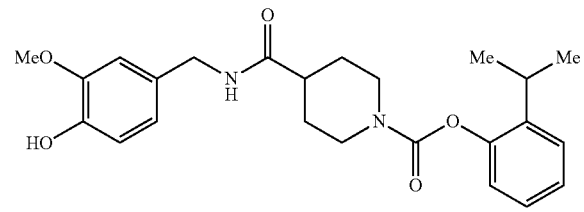

(1) N,N'-carbonyldiimidazol (684 mg) was added to a mixture of N-(4-benzyloxy-3-methoxybenzyl)-4-piperidinecarboxamide hydrochloride (1.50 g) and methylene chloride (25 ml). After stirring the reaction mixture at room temperature for 6 hours, water was added thereto and the mixture was extracted with chloroform. The organic layer was dried over sodium sulfate and the solvent was evaporated under reduced pressure. The residue was dissolved in acetonitrile (10 ml) and methyl iodide was added thereto. After stirring the reaction mixture at room temperature for 20 hours, the solvent was evaporated under reduced pressure to obtain 1.70 g of the product, and 2-isopropylphenol (131 mg), triethylamine (0.13 ml) and acetonitrile (5 ml) were added to 350 mg of the obtained product and the reaction mixture was refluxed with heating for 8 hours. The reaction mixture was evaporated under reduced pressure, and water and chloroform were added thereto. The organic layer was washed with water and then saturated brine, dried over sodium sulfate and the solvent was evaporated under reduced pressure. The residue was purified by silica gel chromatography (elution solvent: chloroform/methanol=100/0 to 90/10 gradient) to obtain 262 mg of 2-isopropylphenyl 4-(4-benzyloxy-3-methoxybenzylcarbamoyl)-piperidine-1-carboxylate.

(2) The product (260 mg) of the above (1) was dissolved in ethanol (5 ml) and 10% palladium on carbon (50 mg) was added thereto to carry out catalytic hydrogenation at room temperature. After 5 hours, the catalyst was filtered, the solvent was evaporated and the residue was purified by silica gel chromatography (elution solvent: chloroform/methanol=100/0 to 90/10 gradient) to obtain 180 mg of an intended product.

$^1$H-NMR (CDCl$_3$, δ): 1.22 (6H, d), 1.70-1.99 (4H, m), 2.28-2.38 (1H, m), 2.80-2.96 (1H, m), 2.99-3.12 (2H, m), 3.88 (3H, s), 4.20-4.39 (2H, m), 4.37 (2H, d), 5.65 (1H, s), 5.77 (1H, brs), 6.77 (1H, dd), 6.80 (1H, d), 6.87 (1H, d), 6.99-7.10 (1H, m), 7.14-7.21 (2H, m), 7.25-7.31 (1H, m).

Examples 42-44

Using various substituted phenols instead of the 2-isopropylphenol in Example 41, the compounds shown in Table 8 were obtained by reacting and treating in the same manner as in Example 41.

TABLE 8

| | Structural formula | $^1$H-NMR (CDCl$_3$, δ) |
|---|---|---|
| Example 42 | | 1.51-1.70 (5H, m), 1.71-1 86 (4H, m), 1.88-2.07 (3H, m), 2.27-2.39 (1H, m), 2.81-2.97 (1H, m), 2.99-3.13 (2H, m), 3.89 (3H, s), 4.22-4.42 (2H, m), 4.38 (2H, d), 5.62 (1H, s), 5.75 (1H, brs), 6.77 (1H, dd), 6.80 (1H, d), 6.88 (1H, d), 7.00-7.14 (1H, m), 7.15-7.20 (2H, m), 7.26-7.31 (1H, m). |

TABLE 8-continued

| | Structural formula | ¹H-NMR (CDCl₃, δ) |
|---|---|---|
| Example 43 | | 1.24 (6H, d), 1.65-1.98 (4H, m), 2.26-2.37 (1H, m), 2.79-3.10 (3H, m), 3.88 (3H, s), 4.21-4.40 (2H, m), 4.38 (2H, d), 5.65 (1H, s), 5.78 (1H, brs), 6.77 (1H, dd), 6.80 (1H, d), 6.87 (1H, d), 6.89-7.00 (3H, m), 7.02-7.10 (1H, m). |
| Example 44 | | 1.23 (6H, d), 1.71-1.86 (4H, m), 2.28-2.38 (1H, m), 2.81-3.10 (3H, m), 3.89 (3H, s), 4.25-4.40 (2H, m), 4.37 (2H, d), 5.62 (1H, s), 5.73 (1H, brs), 6.77 (1H, dd), 6.80 (1H, d), 6.88 (1H, d), 7.00 (2H, d), 7.20 (2H, d). |

Example 45

Preparation of 2-isopropylphenyl 3-(4-hydroxy-3-methoxybenzylcarbamoyl)-azetidine-1-carboxylate

[Chemical Formula 20]

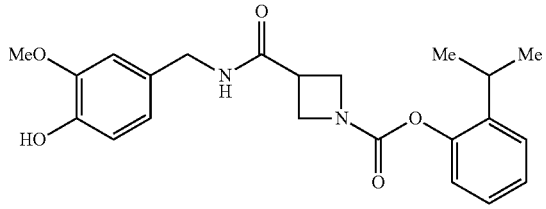

(1) N,N'-carbonyldiimidazol (820 mg) was added to a mixture of N-(4-benzyloxy-3-methoxybenzyl)-3-azetidinecarboxamide hydrochloride (1.50 g) and methylene chloride (25 ml). After stirring the reaction mixture at room temperature for 20 hours, water was added thereto and the mixture was extracted with chloroform. The organic layer was washed with saturated brine, dried over sodium sulfate and the solvent was evaporated under reduced pressure. The residue was purified by silica gel chromatography (elution solvent: chloroform/methanol=100/0 to 90/10 gradient) to obtain 1.37 g of N-(4-benzyloxy-3-methoxybenzyl)-1-(imidazol-1-carbonyl)azetidine-3-carboxamide.

(2) The product (1.37 g) of the above (1) was dissolved in acetonitrile (10 ml) and methyl iodide was added thereto. After stirring the reaction mixture at room temperature for 20 hours, the solvent was evaporated under reduced pressure to obtain 1.81 g of a product, and 2-isopropylphenol (119 mg), triethylamine (0.12 ml) and acetonitrile (5 ml) were added to 350 mg of the obtained product and the reaction mixture was refluxed with heating for 8 hours. The reaction mixture was evaporated under reduced pressure, and water and chloroform were added thereto. The organic layer was washed with water and saturated brine, dried over sodium sulfate and the solvent was evaporated under reduced pressure. The residue was purified by silica gel chromatography (elution solvent: chloroform/methanol=100/0 to 90/10 gradient) to obtain 270 mg of 2-isopropylphenyl 3-(4-benzyloxy-3-methoxybenzylcarbamoyl)-azetidine-1-carboxylate.

(3) The product (260 mg) of the above (2) was dissolved in ethanol (10 ml) and 10% palladium on carbon (60 mg) was added thereto to carry out catalytic hydrogenation at room temperature. After 4 hours, the catalyst was filtered, the solvent was evaporated and the residue was purified by silica gel chromatography (elution solvent: chloroform/methanol=100/0 to 90/10 gradient) to obtain 179 mg of an intended product.

¹H-NMR (CDCl₃, δ): 1.22 (6H, d), 3.05-3.17 (1H, m), 3.23-3.35 (1H, m), 3.89 (3H, s), 4.12-4.35 (3H, m), 4.40 (2H, d), 4.41-4.55 (1H, m), 5.65 (1H, s), 5.79 (1H, brs), 6.77 (1H, dd), 6.80 (1H, d), 6.87 (1H, d), 7.02-7.10 (1H, m), 7.13-7.21 (2H, m), 7.25-7.33 (1H, m).

Example 46

Preparation of 2-cyclopentylphenyl 3-(4-hydroxy-3-methoxybenzylcarbamoyl)-azetidine-1-carboxylate

[Chemical Formula 21]

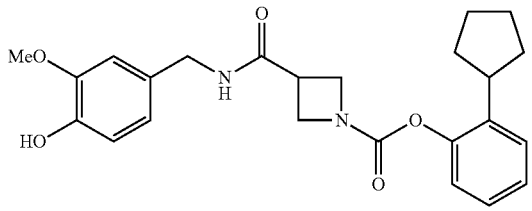

Using 2-cyclopentylphenol instead of the 2-isopropylphenol in Example 45, the reaction and treatment were carried out in the same manner as in Example 45 to obtain an intended product.

¹H-NMR (CDCl₃, δ): 1.51-1.84 (6H, m), 1.93-2.09 (2H, m), 3.06-3.18 (1H, m), 3.21-3.32 (1H, m), 3.88 (3H, s), 4.10-4.32 (3H, m), 4.39 (2H, d), 4.40-4.55 (1H, m), 5.67 (1H, s), 5.86 (1H, brs), 6.77 (1H, dd), 6.81 (1H, d), 6.87 (1H, d), 7.01-7.09 (1H, m), 7.12-7.21 (2H, m), 7.25-7.32 (1H, m).

Example 47

Preparation of (1S*,2S*)-2-methylcyclohexyl 4-(4-hydroxy-3-methoxybenzylcarbamoyl)-piperidine-1-carboxylate

[Chemical Formula 22]

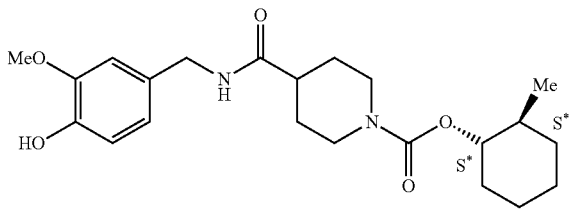

Using (1S*,2S*)-2-methylcyclohexanol instead of cis-4-ethylcyclohexanol in Example 1, the reaction and treatment were carried out in the same manner as in Example 1 to obtain an intended product.

$^1$H-NMR (CDCl$_3$, δ): 0.91 (3H, d), 0.98-1.50 (5H, m), 1.52-2.03 (8H, m), 2.18-2.32 (1H, m), 2.69-2.84 (2H, m), 3.88 (3H, s), 4.12-4.35 (3H, m), 4.36 (2H, d), 5.60 (1H, s), 5.67 (1H, brs), 6.75 (1H, dd), 6.79 (1H, d), 6.87 (1H, d).

Example 48

Preparation of cyclohexyl 4-(4-hydroxy-3-methoxy-benzylcarbamoyl)-piperidine-1-carboxylate

[Chemical Formula 23]

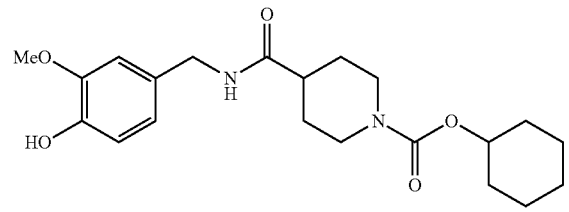

Using cyclohexanol instead of the cis-4-ethylcyclohexanol in Example 1, the reaction and treatment were carried out in the same manner as in Example 1 to obtain an intended product.

$^1$H-NMR (CDCl$_3$, δ): 1.22-1.58 (6H, m), 1.60-1.88 (8H, m), 2.18-2.33 (1H, m), 2.68-2.85 (2H, m), 3.88 (3H, s), 4.10-4.28 (2H, m), 4.35 (2H, d), 4.61-4.73 (1H, m), 5.61 (1H, s), 5.67 (1H, brs), 6.75 (1H, dd), 6.77 (1H, d), 6.86 (1H, d).

Test Example

Hereinafter, the pharmacological test results of the representative compounds of the present invention are shown to describe the pharmacological effects of the compounds of the present invention. However, the present invention is not limited to these test examples.

Test Example 1

Study on Analgesic Effect (Von Frey Filament Test Using Rat Chung Model)

The present test is to measure the analgesic effect based on the improvement level of the mechanical hyperalgesia in a neuropathic pain model as the indicator by transdermally administering the compound of the present invention and was carried out in accordance with the method of Kim and Chung [Pain, 50, 355-363 (1992)] or the method of Tsuda et al. [Nature, 424, 778-783, 2003].

Specifically, using Jcl: Wistar male rat (7 to 9 rats/group, 5 weeks of age at the time of surgery), spinal nerves were injured to induce hyperalgesia and the withdrawal threshold was measured using the von Frey filament. In the surgery, under Pentobarbital anesthesia, the left L5 spinal nerve was exposed, ligated near the spinal cord using a silk suture (5-0) and transected just peripheral to the ligation. After suturing the incision and keeping the rats for 2 weeks, the rats were subjected to the von Frey filament test. The measurement of the mechanical hyperalgesia was carried out by applying von Frey filaments (1.0, 2.0, 4.0, 8.0, 15.0 g) to the plantar surface of the left hindlimb, and the filament intensity at which 50% or higher withdrawal behavior was observed was defined as the withdrawal threshold.

After dissolving the test compounds in a mixture of Tween 80 and ethanol, the obtained solution was mixed with a hydrophilic ointment to prepare a formulation having a concentration of 0.1%. The withdrawal threshold before administering the test compound was measured to define the pre-administration value (100%). Thereafter, once a day, for 2 weeks, the formulation having a concentration of 0.1% was transdermally administered (applied) to the plantar surface of the left hindlimb, the von Frey filament test was carried out on the following day of the last administration to measure the post-administration value. Further, the same formulation as above but free of the test compound was prepared as a vehicle control and the same test was carried out.

The analgesic effect is a relative ratio when a test compound pre-administration value calculated using the following numerical formula is 100%. The pre-administration withdrawal threshold was 3.3±0.1 g (119 cases) (the withdrawal threshold of sham-operated rat was 10 to 15 g).

%=(test compound post-administration withdrawal threshold value/pre-administration withdrawal threshold value)×100

The results are shown in Table 9 below.

TABLE 9

| Example | % to pre-administration value |
|---------|-------------------------------|
| 1 | 220 |
| 8 | 191 |
| 14 | 241 |
| 16 | 218 |
| 35 | 183 |
| 36 | 209 |
| 37 | 236 |
| 38 | 243 |
| vehicle control | 107 |
| Capsaicin | 228 |

As shown in Table 9, the transdermal administration (application) of the compound of the present invention elevated the withdrawal threshold values by about 200% compared with the pre-administration values and the analgesic effect as intense as that of capsaicin was observed.

Test Example 2

Study on Pungency (Eye-wiping Test)

The test is to examine the pungency of the compound of the present invention, and was carried out in accordance with the method by Jancso et al. [Acta. Physiol. Acad. Sci. Hung., 19, 113-131 (1961)] and the method by Szallasi et al. [Brit. J. Pharmacol., 119, 283-290 (1996)]. Specifically, the test compounds were dissolved in physiological saline containing 5% Tween 80 and 5% ethanol to give each (10 or 30 μg/ml) concentration, and one drop of the obtained solution was applied to the eye of a Std: ddy male mouse (5 mice per group, body weight 20 to 30 g) and the number of the protective wiping behavior with the front paws was counted every minute up to 5 minutes after the administration. Then, the average counts in each minute was calculated and the maximum number was defined as the representative value. Further, as vehicle control, the same test was carried out using physiological saline containing 5% Tween 80 and 5% ethanol.

The results are shown in Table 10.

TABLE 10

| Example | Representative value of the counts of protective wiping behavior (Maximum counts, counts/min) | |
|---|---|---|
| | 10 μg/ml | 30 μg/ml |
| 1 | 7.2 | 11.8 |
| 2 | | 8.0 |
| 3 | 8.8 | 12.0 |
| 5 | | 16.6 |
| 7 | | 14.8 |
| 8 | 6.6 | 10.4 |
| 10 | 8.2 | 12.0 |
| 11 | 6.4 | 10.2 |
| 14 | 5.6 | 8.8 |
| 16 | | 10.4 |
| 19 | 4.4 | 9.2 |
| 22 | 7.4 | 10.0 |
| 35 | 8.0 | 11.0 |
| 36 | 7.0 | 12.6 |
| 37 | 6.8 | 10.6 |
| 38 | 6.2 | 10.0 |
| Capsaicin | 20.0 | |
| vehicle control | 1.6 | |

As shown in Table 10, vigorous wiping behavior was observed by dropping 10 μg/ml capsaicin. On the other hand, each compound of Examples shown in Table 10 had fewer counts of the protective wiping behavior even at 30 μg/ml, revealing weak pungency.

Test Example 3

Bone Marrow Micronucleus Test

Each compound of Examples 2, 16 and 37 dissolved in physiological saline containing ethanol and Tween 80 was subcutaneously administered to Crl: CD male rats twice every 24 hours and micronucleus inducing potential was evaluated.

As a result, the compounds of Examples 2, 16 and 37 didn't elevate the frequency of micronucleus-containing immature erythrocyte in the dosage at which fatal cases start occurring and the dosages up thereto, resulting in no micronucleus inducing potential. These findings revealed that the compounds of the present invention don't have genetic toxicity.

Test Example 4

TRPV1 Agonist Activity Measurement Using Intracellular Calcium Level as Biological Activity Indicator: Fluorescence Image Plate Reader (FLIPR) Method The test is to measure the elevation of intracellular calcium level as the indicator of TRPV1 agonist activity of a test compound using cultured rat dorsal root ganglion cells which express TRPV1 abundantly, and carried out in accordance with the method of Jerman et al. (Jerman, J. C. et al., Comparison of effects of anandamide at recombinant and endogenous rat vanilloid receptors. Br J Anaesth, 2002. 89(6): p. 882-7). More specifically, the dorsal root ganglion was removed from a 7 day old Wistar rat, and the cells were isolated by collagenase-trypsin treatment. Subsequently, the primary cells was cultured in a $CO_2$ incubator controlled at 5% $CO_2$ and 37° C. for 2 days. The culture medium used was Neurobasal™ medium supplemented with L-glutamine, nerve growth factor, N-2-Supplement, Penicillin-Streptomycin, 5-Fluoro-2'-deoxyuridine (culture day 1 only) were added to.

FLIPR$^{TETRA}$ system (Molecular Devices Corp.) was used to measure the intracellular calcium concentration. As an indicator of TRPV1 agonistic activity, the fluorescence intensity elevation was monitored when a test compound is applied to the rat dorsal root ganglion primary culture cells loaded with a calcium-sensitive fluorescent reagent. The results are shown in Table 11.

TABLE 11

| Example (1 μM) | Value (%) when fluorescence intensity for capsaicin (1 μM) is 100% |
|---|---|
| 1 | 87 |
| 2 | 84 |
| 3 | 80 |
| 4 | 80 |
| 5 | 84 |
| 6 | 80 |
| 7 | 90 |
| 8 | 96 |
| 9 | 83 |
| 10 | 92 |
| 11 | 94 |
| 12 | 92 |
| 13 | 81 |
| 14 | 78 |
| 15 | 83 |
| 16 | 84 |
| 17 | 82 |
| 18 | 86 |
| 19 | 84 |
| 20 | 73 |
| 21 | 85 |
| 22 | 80 |
| 23 | 77 |
| 24 | 84 |
| 25 | 71 |
| 26 | 82 |
| 27 | 86 |
| 28 | 81 |
| 29 | 83 |
| 30 | 78 |
| 31 | 68 |

TABLE 11-continued

| Example (1 μM) | Value (%) when fluorescence intensity for capsaicin (1 μM) is 100% |
|---|---|
| 32 | 78 |
| 33 | 73 |
| 34 | 72 |
| 35 | 86 |
| 36 | 104 |
| 37 | 101 |
| 38 | 97 |
| 39 | 91 |
| 40 | 91 |
| 41 | 83 |
| 42 | 72 |
| 43 | 68 |
| 44 | 83 |
| 45 | 72 |
| 46 | 68 |
| 47 | 85 |
| 48 | 77 |
| Vehicle control | 0 |
| Capsaicin | 100% |

As shown in Table 11, the compounds of the present invention induced the elevation of the intracellular calcium level as does capsaicin, which is the TRPV1 agonist.

Test Example 5

Study on Analgesic Effect in Combination with Epilepsy/Neuropathic Pain Therapeutic Agent Pregabalin (Von Frey Filament Test Using Rat Chung Model)

The study was conducted using the same methods and evaluation criteria as in Test Example 1 with the exception of the administration route of the test compounds (see Test Example 1).

Using the von Frey filaments the test compound pre-administration values (pressure withdrawal threshold) were measured. Subsequently, 50 μl of a solution containing a test compound or vehicle control was intraplantarly injected to the left hindlimb using a microsyringe (intraplantar injection: i. pl. administration), and on the following day the withdrawal threshold was measured (effect of the test compound alone). Thereafter, 10 mg/kg of Pregabalin was orally administered and an hour later the withdrawal threshold was measured (combined effect).

The test compound was dissolved in physiological saline containing Tween 80 and ethanol to give a concentration of 0.1% (W/V). Pregabalin was dissolved in distilled water. Physiological saline containing Tween 80 and ethanol was used as the vehicle control for the i. pl. administration.

The analgesic effect is a relative ratio when a pre-administration value calculated using the following numerical formula is 100%. The test compound pre-administration withdrawal threshold was 3.9±0.5 g (32 cases) (the withdrawal threshold of sham-operated rat was 10 to 15 g).

%=(test compound post-administration withdrawal threshold value/pre-administration withdrawal threshold value)×100    (1)

%=(test compound and Pregabalin post-administration withdrawal threshold value/pre-administration escape threshold value)×100    (2)

The results are shown in Table 12 below.

TABLE 12

| | % to pre-administration value | |
|---|---|---|
| Example | (1) Test compound post-i. pl. administration value | (2) Pregabalin post-oral administration value (Test compound or vehicle control administered on the day before) |
| Vehicle | 113% | 125% |
| 8 | 197% | 244% |
| 16 | 200% | 223% |
| 37 | 169% | 219% |

As shown in Table 12, the phenomenon was observed wherein the withdrawal threshold values were higher when the compound of the present invention was combined with Pregabalin than when Pregabalin or the test compound was administered alone. More specifically, the additive and synergistic analgesic effects can be expected by combining Pregabalin with the compound of the present invention.

Industrial Applicability

The compounds of the present invention and physiologically acceptable salts thereof, which have strong analgesic effects and less pungency than capsaicin, are hence useful as an analgesic and anti-inflammatory drug and also as a therapeutic drug for the pains caused by various types of neuropathic pains such as diabetic neuropathy pain, postherpetic neuralgia, trigeminal neuralgia and HIV-polyneuropathy pain to begin with, and pains caused by rheumatoid arthritis and osteoarthritis which are not sufficiently treated with the existing analgesics. Further, the compounds are also useful as a preventive and/or therapeutic drug for migraine headache or cluster headache, pruritus, allergic or non-allergic rhinitis, overactive bladder, stroke, irritable bowel syndrome, respiratory diseases such as asthma/chronic obstructive pulmonary disease, dermatitis, mucositis, gastroduodenal ulcer, inflammatory bowel syndrome, diabetes and obesity.

The invention claimed is:

1. A compound represented by the following formula (I):

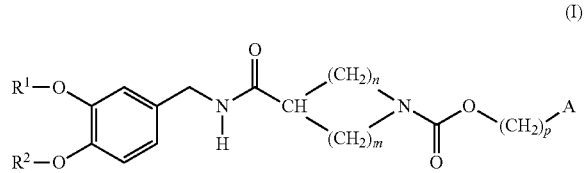

wherein $R^1$ represents a methyl group or a hydrogen atom, $R^2$ represents a hydrogen atom, a $C_{1-4}$ alkyl group, a $C_{1-4}$ alkylcarbonyl group or an aryl carbonyl group, A represents a $C_{3-8}$ cycloalkyl group, a $C_{3-8}$ cycloalkenyl group, an aryl group or a heteroaryl group, wherein each group may be substituted at a position substitutable with $C_{1-6}$ alkyl, $C_{2-6}$ alkenyl, $C_{3-8}$ cycloalkyl or halogen, n and m, the same or different, each represent an integer of 1, 2 or 3, p represents an integer of 0 or 1, or a physiologically acceptable salt thereof.

2. The compound according to claim 1, wherein, in the formula (I), A represents a $C_{3-8}$ cycloalkyl group or an aryl group, wherein each group may be substituted with 1 to 5 same or different substituents selected from the group consisting of $C_{1-6}$ alkyl, $C_{2-6}$ alkenyl, $C_{3-8}$ cycloalkyl and halogen, or a physiologically acceptable salt thereof.

3. The compound according to claim 1, wherein, in the formula (I), A represents a $C_{3-8}$ cycloalkyl group or an aryl group, wherein each group may be substituted with 1 to 5 same or different substituents selected from the group consisting of $C_{1-6}$ alkyl, $C_{2-6}$ alkenyl and $C_{3-8}$ cycloalkyl, or a physiologically acceptable salt thereof.

4. The compound according to claim 1, wherein, in the formula (I), n and m, the same or different, each represent an integer of 1 or 2, or a physiologically acceptable salt thereof.

5. The compound according to claim 4, wherein, in the formula (I), n and m are both 2, or a physiologically acceptable salt thereof.

6. The compound according to claim 1, wherein, in the formula (I), p represents an integer of 0, or a physiologically acceptable salt thereof.

7. The compound according to claim 1, wherein, in the formula (I), $R^1$ represents a methyl group, or a physiologically acceptable salt thereof.

8. The compound according to claim 1, wherein, in the formula (I), $R^2$ represents a hydrogen atom, or a physiologically acceptable salt thereof.

9. The compound according to claim 1 represented by the formula (I) selected from the group consisting of
   4-ethylcyclohexyl 4-(4-hydroxy-3-methoxybenzylcarbamoyl)-piperidine-1-carboxylate,
   4,4-dimethylcyclohexyl 4-(4-hydroxy-3-methoxybenzylcarbamoyl)-piperidine-1-carboxylate,
   3-methylcyclohexyl 4-(4-hydroxy-3-methoxybenzylcarbamoyl)-piperidine-1-carboxylate,
   2-methylcyclohexyl 4-(4-hydroxy-3-methoxybenzylcarbamoyl)-piperidine-1-carboxylate,
   4,4-diethylcyclohexyl 3-(4-hydroxy-3-methoxybenzylcarbamoyl)-azetidine-1-carboxylate,
   4-t-butylcyclohexyl 3-(4-hydroxy-3-methoxybenzylcarbamoyl)-azetidine-1-carboxylate,
   4-t-butylcyclohexyl 3-(4-hydroxy-3-methoxybenzylcarbamoyl)-pyrrolidine-1-carboxylate,
   4-methylcyclohexyl 4-(4-hydroxy-3-methoxybenzylcarbamoyl)-piperidine-1-carboxylate,
   3,3,5,5-tetramethylcyclohexyl 3-(4-hydroxy-3-methoxybenzylcarbamoyl)-azetidine-1-carboxylate,
   2-isopropyl-5-methylcyclohexyl 3-(4-hydroxy-3-methoxybenzylcarbamoyl)-azetidine-1-carboxylate,
   4-ethylcyclohexyl 3-(4-hydroxy-3-methoxybenzylcarbamoyl)-pyrrolidine-1-carboxylate,
   4,4-dimethylcyclohexyl 3-(4-hydroxy-3-methoxybenzylcarbamoyl)-pyrrolidine-1-carboxylate,
   4,4-diethylcyclohexyl 3-(4-hydroxy-3-methoxybenzylcarbamoyl)-pyrrolidine-1-carboxylate,
   4-t-butylcyclohexyl 4-(4-hydroxy-3-methoxybenzylcarbamoyl)-piperidine-1-carboxylate,
   4-butylcyclohexyl 3-(4-hydroxy-3-methoxybenzylcarbamoyl)-azetidine-1-carboxylate,
   4,4-diethylcyclohexyl 4-(4-hydroxy-3-methoxybenzylcarbamoyl)-piperidine-1-carboxylate,
   3,5-dimethylcyclohexyl 4-(4-hydroxy-3-methoxybenzylcarbamoyl)-piperidine-1-carboxylate,
   2-ethylcyclohexyl 4-(4-hydroxy-3-methoxybenzylcarbamoyl)-piperidine-1-carboxylate,
   4-ethylcyclohexyl 3-(4-hydroxy-3-methoxybenzylcarbamoyl)-azetidine-1-carboxylate,
   3-methylcyclohexyl 3-(4-hydroxy-3-methoxybenzylcarbamoyl)-azetidine-1-carboxylate,
   4-isopropylcyclohexyl 3-(4-hydroxy-3-methoxybenzylcarbamoyl)-azetidine-1-carboxylate,
   2-isopropenyl-5-methylcyclohexyl 3-(4-hydroxy-3-methoxybenzylcarbamoyl)-azetidine-1-carboxylate,
   cycloheptyl 4-(4-hydroxy-3-methoxybenzylcarbamoyl)-piperidine-1-carboxylate,
   cyclohexylmethyl 4-(4-hydroxy-3-methoxybenzylcarbamoyl)-piperidine-1-carboxylate,
   2-isopropylphenyl 4-(4-hydroxy-3-methoxybenzylcarbamoyl)-piperidine-1-carboxylate,
   2-cyclopentylphenyl 4-(4-hydroxy-3-methoxybenzylcarbamoyl)-piperidine-1-carboxylate,
   3-isopropylphenyl 4-(4-hydroxy-3-methoxybenzylcarbamoyl)-piperidine-1-carboxylate,
   4-isopropylphenyl 4-(4-hydroxy-3-methoxybenzylcarbamoyl)-piperidine-1-carboxylate,
   2-isopropylphenyl 3-(4-hydroxy-3-methoxybenzylcarbamoyl)-azetidine-1-carboxylate,
   2-cyclopentylphenyl 3-(4-hydroxy-3-methoxybenzylcarbamoyl)-azetidine-1-carboxylate, and
   cyclohexyl 4-(4-hydroxy-3-methoxybenzylcarbamoyl)-piperidine-1-carboxylate, or a physiologically acceptable salt thereof.

10. The compound according to claim 1 represented by the formula (I) selected from the group consisting of
   cis-4-ethylcyclohexyl 4-(4-hydroxy-3-methoxybenzylcarbamoyl)-piperidine-l-carboxylate,
   trans-4-ethylcyclohexyl 4-(4-hydroxy-3-methoxybenzylcarbamoyl)-piperidine-l-carboxylate,
   4,4-dimethylcyclohexyl 4-(4-hydroxy-3-methoxybenzylcarbamoyl)-piperidine-l-carboxylate,
   trans-3-methylcyclohexyl 4-(4-hydroxy-3-methoxybenzylcarbamoyl)-piperidine-l-carboxylate,
   cis-2-methylcyclohexyl 4-(4-hydroxy-3-methoxybenzylcarbamoyl)-piperidine-1-carboxylate,
   4,4-diethylcyclohexyl 3-(4-hydroxy-3-methoxybenzylcarbamoyl)-azetidine-1-carboxylate,
   cis-4-t-butylcyclohexyl 3-(4-hydroxy-3-methoxybenzylcarbamoyl)-azetidine-1-carboxylate,
   cis-4-t-butylcyclohexyl (S)-3-(4-hydroxy-3-methoxybenzylcarbamoyl)-pyrrolidine-1-carboxylate,
   cis-4-methylcyclohexyl 4-(4-hydroxy-3-methoxybenzylcarbamoyl)-piperidine-1-carboxylate,
   3,3,5,5-tetramethylcyclohexyl 3-(4-hydroxy-3-methoxybenzylcarbamoyl)-azetidine-1-carboxylate,
   (1S,2S,5R)-2-isopropyl-5-methylcyclohexyl 3-(4-hydroxy-3-methoxybenzylcarbamoyl)-azetidine-1-carboxylate,
   cis-4-ethylcyclohexyl (S)-3-(4-hydroxy-3-methoxybenzylcarbamoyl)-pyrrolidine-1-carboxylate,
   4,4-dimethylcyclohexyl (S)-3-(4-hydroxy-3-methoxybenzylcarbamoyl)-pyrrolidine-1-carboxylate, and
   4,4-diethylcyclohexyl (S)-3-(4-hydroxy-3-methoxybenzylcarbamoyl)-pyrrolidine-1-carboxylate, or a physiologically acceptable salt thereof.

11. The compound according to claim 1 represented by the formula (I) selected from the group consisting of
   cis-4-ethylcyclohexyl 4-(4-hydroxy-3-methoxybenzylcarbamoyl)-piperidine-1-carboxylate,
   trans-4-ethylcyclohexyl 4-(4-hydroxy-3-methoxybenzylcarbamoyl)-piperidine-1-carboxylate,
   4,4-dimethylcyclohexyl 4-(4-hydroxy-3-methoxybenzylcarbamoyl)-piperidine-1-carboxylate,
   trans-3-methylcyclohexyl 4-(4-hydroxy-3-methoxybenzylcarbamoyl)-piperidine-1-carboxylate,
   cis-2-methylcyclohexyl 4-(4-hydroxy-3-methoxybenzylcarbamoyl)-piperidine-1-carboxylate,
   4,4-diethylcyclohexyl 3-(4-hydroxy-3-methoxybenzylcarbamoyl)-azetidine-1-carboxylate,
   cis-4-t-butylcyclohexyl 3-(4-hydroxy-3-methoxybenzylcarbamoyl)-azetidine-1-carboxylate, cis-4-t-butylcyclohexyl (S)-3-(4-hydroxy-3-methoxybenzylcarbamoyl)-pyrrolidine-1-carboxylate,
cis-4-methylcyclohexyl 4-(4-hydroxy-3-methoxybenzylcarbamoyl)-piperidine-1-carboxylate,
trans-4-methylcyclohexyl 4-(4-hydroxy-3-methoxybenzylcarbamoyl)-piperidine-1-carboxylate,
cis-4-t-butylcyclohexyl 4-(4-hydroxy-3-methoxybenzylcarbamoyl)-piperidine-1-carboxylate,
cycloheptyl 4-(4-hydroxy-3-methoxybenzylcarbamoyl)-piperidine-1-carboxylate,
cyclohexylmethy 4-(4-hydroxy-3-methoxybenzylcarbamoyl)-piperidine-1-carboxylate,
cis-3-methylcyclohexyl 4-(4-hydroxy-3-methoxybenzylcarbamoyl)-piperidine-1-carboxylate,
trans-2-methylcyclohexyl 4-(4-hydroxy-3-methoxybenzylcarbamoyl)-piperidine-1-carboxylate,
trans-4-t-butylcyclohexyl 3-(4-hydroxy-3-methoxybenzylcarbamoyl)-azetidine-1-carboxylate,
3,3,5,5-tetramethylcyclohexyl 3-(4-hydroxy-3-methoxybenzylcarbamoyl)-azetidine-1-carboxylate,
cis-4-butylcyclohexyl 3-(4-hydroxy-3-methoxybenzylcarbamoyl)-azetidine-1-carboxylate,
cyclohexyl 4-(4-hydroxy-3-methoxybenzylcarbamoyl)-piperidine-1-carboxylate, or a physiologically acceptable salt thereof.

12. A pharmaceutical composition comprising the compound according to claim 1 or the physiologically acceptable salt thereof as an active ingredient, and a pharmaceutically acceptable carrier.

13. A method for treating pain and/or inflammation comprising administrating to a patient an effective amount of the compound according to claim 1 or the physiologically acceptable salt thereof.

14. A pharmaceutical comprising:
the compound according to claim 1 or the physiologically acceptable salt thereof; and
at least one other drug selected from the group consisting of a narcotic analgesic, a neuropathic pain therapeutic agent, a non-steroidal anti-inflammatory drug, a steroidal anti-inflammatory drug, an antidepressant, an antiepileptic drug, an antispasmogenic, an anesthetic, an antiarrhythmic drug, a local anesthetic and an anti-anxiety drug.

15. A pharmaceutical composition comprising the pharmaceutical according to claim 14 as an active ingredient, and a pharmaceutically acceptable carrier.

16. A method for treating pain and/or inflammation comprising administering to a patient an effective amount of the pharmaceutical according to claim 14.

17. A compound, which is
(1 R,2S)-2-methylcyclohexyl 4-(4-hydroxy-3-methoxybenzylcarbamoyl)-piperidine-1-carboxylate.

18. A pharmaceutical composition comprising the compound according to claim 17, and a pharmaceutically acceptable carrier.

19. A method for treating pain and/or inflammation comprising administrating to a patient an effective amount of the compound according to claim 17.

* * * * *